United States Patent
Sommen et al.

(10) Patent No.: US 8,921,517 B2
(45) Date of Patent: Dec. 30, 2014

(54) PROCESS FOR THE PRODUCTION OF BIVALIRUDIN

(75) Inventors: Geoffroy Sommen, Braine l'Alleud (BE); Luciano Forni, La Louvriére (BE)

(73) Assignee: Lonza Braine SA, Braine-l'Alleud (BE)

( * ) Notice: Subject to any disclaimer, the term of this patent is extended or adjusted under 35 U.S.C. 154(b) by 170 days.

(21) Appl. No.: 13/139,956

(22) PCT Filed: Dec. 17, 2009

(86) PCT No.: PCT/EP2009/009080
§ 371 (c)(1),
(2), (4) Date: Jun. 15, 2011

(87) PCT Pub. No.: WO2010/075983
PCT Pub. Date: Jul. 8, 2010

(65) Prior Publication Data
US 2011/0251372 A1    Oct. 13, 2011

Related U.S. Application Data

(60) Provisional application No. 61/260,471, filed on Nov. 12, 2009.

(30) Foreign Application Priority Data

Dec. 29, 2008 (EP) .................................... 08022479

(51) Int. Cl.
C07K 14/815 (2006.01)
C07K 7/08 (2006.01)
C07K 5/107 (2006.01)

(52) U.S. Cl.
CPC ............. C07K 14/815 (2013.01); C07K 5/1016 (2013.01)
USPC ............ 530/326; 530/328; 530/329; 530/330

(58) Field of Classification Search
None
See application file for complete search history.

(56) References Cited

U.S. PATENT DOCUMENTS

| 5,196,404 | A | 3/1993 | Maraganore et al. |
| 8,252,896 | B2 * | 8/2012 | Hsiao et al. .................. 530/326 |
| 2007/0093423 | A1 * | 4/2007 | Tovi et al. ...................... 514/13 |

FOREIGN PATENT DOCUMENTS

| WO | 9102750 A1 | 3/1991 |
| WO | 9850563 A1 | 11/1998 |
| WO | 2007033383 A2 | 3/2007 |
| WO | 2007033383 A3 | 3/2007 |
| WO | WO2006081249 A2 | 1/2008 |
| WO | 2010028122 A1 | 3/2010 |

OTHER PUBLICATIONS

Tatsu et al.,"Caged Compounds and Solid-Phase Synthesis", in Dynamic Studies in Biology, Edited by M. Goeldner, R. Givens, 2005, pp. 131-154.*
Benoiton, "Chemistry of Peptide Synthesis, Chapter 3: Protectors and Methods of Deprotection"; 2005; pp. 65-91.*
Vincent Bille, "Peptide API's Manufacturing Scaling-Up Downstream Processing", UCB-Bioproducts, TIDES 2001-Tucson, AZ.
Okayama, et al., "Anticoagulant Peptides; Synthesis, Stability and Antithrombin Activity of Hirudin C-Terminal-Related Peptides and Their Disulfated Analog", Chemical and Pharmaceutical Bulletin, vol. 44, No. 7, pp. 1344-1350; 1996.
Kun-Hwa Hsieh, "Localization of an Effective Fibrin β-Chain Polymerization Site: Implications for the Polymerization Mechanism", Biochemistry, vol. 36, pp. 9381-9387; 1997.
Steinmetzer, et al., "Design and Evaluation of Novel Bivalent Thrombin Inhibitors Based on Amidinophenylalanines", Eur. Journal of Biochemistry, vol. 265, pp. 598-605; 1999.
Bonora, et al., "Linear Oligopeptides LXXIV. Synthesis, Characterization, and Conformational Analysis of a Series of Monodispersed Homopeptides (Up to the Nonamer) of Glycine" Gazzetta Chimica Italiana, vol. 110, pp. 503-510; 1980.
Japanese Biochemical Society—New Biochemical Experiment Course I—Protein VI—Mar. 29, 1992—Complete Translation of Ref 02; 35 pages.

* cited by examiner

*Primary Examiner* — Karlheinz R Skowronek
*Assistant Examiner* — Lianko Garyu
(74) *Attorney, Agent, or Firm* — Hoffmann & Baron, LLP

(57) ABSTRACT

The present invention relates to a process for the production of bivalirudin, a 20-mer peptide of formula H-(D)-Phe-Pro-Arg-Pro-Gly-Gly-Gly-Asn-Gly-Asp-Phe-Glu-Glu-Ile-Pro-Glu-Glu-Tyr-Leu-OH (SEQ ID NO: 1).

18 Claims, No Drawings

SEQUENCE LISTING

<160> NUMBER OF SEQ ID NOS: 10

<210> SEQ ID NO 1
<211> LENGTH: 20
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: D enantiomer of Phe (D-Phe)

<400> SEQUENCE: 1

Phe Pro Arg Pro Gly Gly Gly Gly Asn Gly Asp Phe Glu Glu Ile Pro
1               5                   10                  15

Glu Glu Tyr Leu
            20

<210> SEQ ID NO 2
<211> LENGTH: 10
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: D enantiomer of Phe (D-Phe)

<400> SEQUENCE: 2

Phe Pro Arg Pro Gly Gly Gly Gly Asn Gly
1               5                   10

<210> SEQ ID NO 3
<211> LENGTH: 10
<212> TYPE: PRT
<213> ORGANISM: Artificial
<220> FEATURE:
<223> OTHER INFORMATION: Synthetic construct

<400> SEQUENCE: 3

Asp Phe Glu Glu Ile Pro Glu Glu Tyr Leu
1               5                   10

<210> SEQ ID NO 4
<211> LENGTH: 4
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: D enantiomer of Phe (D-Phe)

<400> SEQUENCE: 4

Phe Pro Arg Pro
1

<210> SEQ ID NO 5
<211> LENGTH: 6
<212> TYPE: PRT
<213> ORGANISM: Artificial
<220> FEATURE:
<223> OTHER INFORMATION: Synthetic construct

<400> SEQUENCE: 5

```
Gly Gly Gly Gly Asn Gly
1               5

<210> SEQ ID NO 6
<211> LENGTH: 4
<212> TYPE: PRT
<213> ORGANISM: Artificial
<220> FEATURE:
<223> OTHER INFORMATION: Synthetic construct

<400> SEQUENCE: 6

Glu Glu Tyr Leu
1

<210> SEQ ID NO 7
<211> LENGTH: 4
<212> TYPE: PRT
<213> ORGANISM: Artificial
<220> FEATURE:
<223> OTHER INFORMATION: Synthetic construct

<400> SEQUENCE: 7

Glu Glu Ile Pro
1

<210> SEQ ID NO 8
<211> LENGTH: 8
<212> TYPE: PRT
<213> ORGANISM: Artificial
<220> FEATURE:
<223> OTHER INFORMATION: Synthetic construct

<400> SEQUENCE: 8

Glu Glu Ile Pro Glu Glu Tyr Leu
1               5

<210> SEQ ID NO 9
<211> LENGTH: 9
<212> TYPE: PRT
<213> ORGANISM: Artificial
<220> FEATURE:
<223> OTHER INFORMATION: Synthetic construct

<400> SEQUENCE: 9

Phe Glu Glu Ile Pro Glu Glu Tyr Leu
1               5

<210> SEQ ID NO 10
<211> LENGTH: 4
<212> TYPE: PRT
<213> ORGANISM: Artificial
<220> FEATURE:
<223> OTHER INFORMATION: Synthetic construct

<400> SEQUENCE: 10

Gly Gly Gly Gly
1
```

PROCESS FOR THE PRODUCTION OF BIVALIRUDIN

This application is the U.S. National Phase of, and Applicants claim priority from, International Patent Application Number PCT/EP2009/009080 filed Dec. 17, 2009, United States Provisional Patent Application bearing Ser. No. 61/260,471 filed Nov. 12, 2009, and European Patent Application bearing Ser. No. 08022479.3 filed Dec. 29, 2008, which are incorporated herein by reference in their entirety.

BACKGROUND OF THE INVENTION

The present invention relates to a novel convergent synthesis of bivalirudin, which is a 20-mer peptide of formula

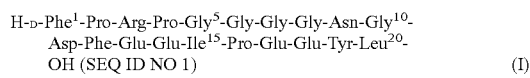
OH (SEQ ID NO 1)                          (I)

The invention further relates to several protected peptides as intermediates in the synthesis of bivalirudin.

Proteolytic processing by thrombin is pivotal in the control of blood clotting. Hirudin, a potential clinical thrombin peptide inhibitor, consists of 65 amino acids. But also shorter peptide segments have proven effective for the treatment of thrombosis, a life threatening condition.

U.S. Pat. No. 5,196,404 discloses, among others, bivalirudin, one of these shorter peptides, which are potent thrombin inhibitors. Bivalirudin is also known as hirulog-8, BG-8967, Efludan, Angiomax® or Hirulog® and possess the amino acid sequence given in formula I.

WO 98/50563 describes a method for the preparation of various peptides, including bivalirudin, by recombinant technology. The method comprises expressing the peptide as part of a fusion protein, followed by release of the peptide from the fusion protein by an acyl acceptor.

Okayama et al. *Chem. Pharm. Bull.* 1996, 44, 1344-1350, and Steinmetzer et al. *Eur. J. Biochem.* 1999, 265, 598-605, devise a solid phase synthesis of different hirulogs on Wang resin. The Wang resin requires cleavage of the peptide from the resin with concentrated trifluoroacetic acid. In a similar solid phase synthesis approach for the preparation of bivalirudin, WO 91/02750 discloses a sequential approach of attaching single Boc-protected amino acids to Boc-L-leucine-o-divinylbenzene resin, followed by simultaneous deprotection and detachment using HF/p-cresol/ethyl methyl sulfate and subsequent lyophilisation and purification. In both cases, the cleavage of the peptide from the resin requires aggressive acidic conditions, which are likely to cause concomitant global deprotection and might result in undesired side reactions with amino acid residues, thus negatively affecting product purity. Moreover, side-reactions often arise in solid phase synthesis by misincorporation, double-hits of single amino acids and/or racemization and lead to side-products which have a structure very similar to that of the target peptide. Purification is therefore awkward and results in loss of yield. Especially longer peptides are prone to adopt an irregular conformation while still attached to the solid support, which makes it even more difficult to attach additional amino acids to the growing chain. Therefore, this problem increases as the length of the peptide increases.

WO 2007/033383 discloses a method for the production of bivalirudin based on a solid phase synthesis or a combination of solid phase and solution synthesis (mixed approach). In one embodiment, the bivalirudin peptide sequence is prepared on a hyper acid-labile resin. In another embodiment, bivalirudin is prepared by coupling a side chain protected N-terminal peptide fragment with a side chain protected C-terminal peptide fragment and subsequent deprotection using strongly acidic conditions. In this case, said N-terminal fragments and the precursor of said C-terminal fragment (i.e. peptide sequence minus Leu) are both prepared by solid phase synthesis. One of the disadvantages of this strategy is substantial formation of D-Tyr$^{19}$-bivalirudin. This impurity is difficult to remove, thus requiring extra efforts, costs and loss in yield to get the purified product. In addition, the amount of purified bivalirudin obtained in the examples of WO 2007/033383 is only in the range of grams, indicating that this approach is not suitable for production of bivalirudin on large scale with good purity.

DESCRIPTION OF THE INVENTION

It is an object of the present invention to provide a more efficient synthesis of bivalirudin that overcomes the known drawbacks of linear, solid phase synthesis and is suitable for the production on an industrial scale.

The present invention relates to a process following a convergent approach, i.e. individual fragments are synthesized separately and then coupled in solution phase to build the desired peptide. The challenge of convergent synthesis is to find suitable fragments and their coupling order for overcoming the known drawbacks of convergent synthesis. These drawbacks are solubility problems during coupling and isolation, lower reaction rates compared to solid phase synthesis and a much higher racemization risk of the C-terminal fragment during coupling. Bivalirudin consists of twenty amino acid residues so that a huge number of possible fragments and coupling orders exist. In addition, bivalirudin contains seven amino acid residues, namely -Arg$^3$-, -Asn$^9$-, -Asp$^{11}$-, -Glu$^{13}$-, -Glu$^{14}$-, -Glu$^{17}$- and -Glu$^{18}$-, all of which have reactive side chain functions that require suitable protection and deprotection. The same applies to suitable protection and deprotection of the N- and C-terminus of the single fragments, thus increasing the challenge of finding a route which achieves the object of the present invention.

Applicant has surprisingly found that bivalirudin of formula I can be advantageously build up by the [(1+2)+(3+{4+5})] strategy as defined below. The numbers 1, 2 and 5 stand for the three peptide fragments of formula V, VI and X, the number 3 stands for the aspartic acid derivative of formula XIII, and the number 4 stands for the phenylalanine derivative of formula XI. The present invention relates to a process for the production of bivalirudin of formula I in solution phase which comprises the steps of (a) reacting an optionally side chain-protected peptide of formula

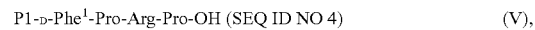
P1-D-Phe$^1$-Pro-Arg-Pro-OH (SEQ ID NO 4)           (V), wherein P1 is a protecting group,
with an optionally side chain-protected peptide of formula

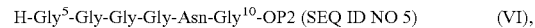
H-Gly$^5$-Gly-Gly-Gly-Asn-Gly$^{10}$-OP2 (SEQ ID NO 5)     (VI), wherein P2 is a protecting group,
to produce an optionally side chain-protected peptide of formula

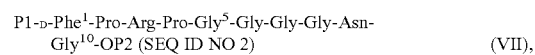
P1-D-Phe$^1$-Pro-Arg-Pro-Gly$^5$-Gly-Gly-Gly-Asn-Gly$^{10}$-OP2 (SEQ ID NO 2)    (VII), wherein P1 and P2 are as defined above,
(b) removing P2 of the peptide produced in step (a) to produce the optionally side chain-protected peptide of formula

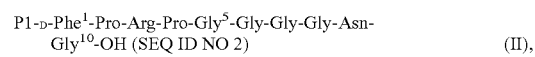
P1-D-Phe$^1$-Pro-Arg-Pro-Gly$^5$-Gly-Gly-Gly-Asn-Gly$^{10}$-OH (SEQ ID NO 2)     (II), wherein P1 is as defined above,
(c) reacting a side chain-protected peptide of formula

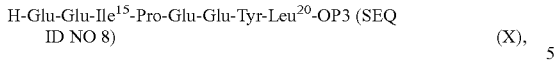

wherein P3 is a protecting group,
with a phenylalanine of formula

P4-Phe$^{12}$-OH     (XI), wherein P4 is a protecting group,
to produce a side chain-protected peptide of formula

wherein P3 and P4 are as defined above,
(d) removing P4 of the peptide produced in step (c) to produce the corresponding N-terminally deprotected, side chain protected peptide of formula XII,
(e) reacting the peptide of formula XII produced in step (d) with a side chain protected aspartic acid of formula P5-Asp$^{11}$-OH     (XIII), wherein P5 is a protecting group,
to produce a side chain-protected peptide of formula

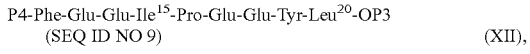

wherein P3 and P5 are as defined above,
(f) removing P5 of the peptide produced in step (e) to produce the side chain-protected peptide of formula

wherein P3 is as defined above,
(g) reacting the optionally side chain-protected peptide of formula II produced in step (b) with the side chain-protected peptide of formula III produced in step (f) to produce a side chain-protected peptide of formula

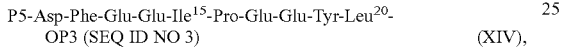

wherein P1 and P3 are as defined above,
(h) removing P1, P3 and the side chain protecting groups of the peptide produced in step (g) to produce bivalirudin of formula I.

The process of the present invention allows for a very efficient synthesis of bivalirudin via a convergent fragment synthesis, which can easily be adapted to the production on an industrial scale.

The C-terminal protecting groups P2 (for peptide VI) and P3 (for peptide X) may be any protecting group which is in line with the orthogonality of the other protecting groups. Suitable examples are C-terminal protecting groups being removable by saponification like methyl (Me) or ethyl (Et) or C-terminal protecting groups being removable by catalytic hydrogenation.

In an embodiment of the process of the present invention, in step (a), the protecting group P1 is a protecting group being stable to catalytic hydrogenation and the protecting group P2 is a protecting group being removable by catalytic hydrogenation and being orthogonal to the optional side chain protecting group(s); in step (c), the protecting group P3 is a protecting group being removable by catalytic hydrogenation and the protecting group P4 is a protecting group being orthogonal to the side chain protecting group(s) of the peptide of formula X and to P3; and in step (e), the protecting group P5 is a protecting group being orthogonal to the side chain protecting group(s) of the peptide/amino acid of formula XII and XIII and to P3, affording a solution phase process comprising the steps of (a) reacting an optionally side chain-protected peptide of formula P1-D-Phe$^1$-Pro-Arg-Pro-OH (SEQ ID NO 4)     (V), wherein P1 is a protecting group being stable to catalytic hydrogenation,
with an optionally side chain-protected peptide of formula H-Gly$^5$-Gly-Gly-Gly-Asn-Gly$^{10}$-OP2 (SEQ ID NO 5)     (VI), wherein P2 is a protecting group being removable by catalytic hydrogenation and being orthogonal to the optional side chain protecting group(s),
to produce an optionally side chain-protected peptide of formula

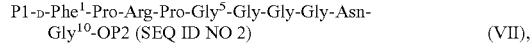

wherein P1 and P2 are as defined above,
(b) removing P2 of the peptide produced in step (a) to produce the optionally side chain-protected peptide of formula

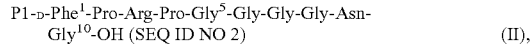

wherein P1 is as defined above,
(c) reacting a side chain-protected peptide of formula

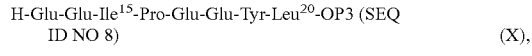

wherein P3 is a protecting group being removable by catalytic hydrogenation, with a phenylalanine of formula P4-Phe$^{12}$-OH     (XI), wherein P4 is a protecting group being orthogonal to the side chain protecting group(s) of the peptide of formula X and to P3,
to produce a side chain-protected peptide of formula

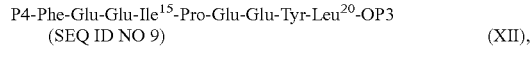

wherein P3 and P4 are as defined above,
(d) removing P4 of the peptide produced in step (c) to produce the corresponding N-terminally deprotected, side chain protected peptide of formula XII,
(e) reacting the peptide of formula XII produced in step (d) with a side chain protected aspartic acid of formula P5-Asp$^{11}$-OH     (XIII), wherein P5 is a protecting group being orthogonal to the side chain protecting group(s) of the peptide/amino acid of formula XII and XIII and to P3,
to produce a side chain-protected peptide of formula

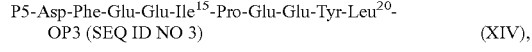

wherein P3 and P5 are as defined above,
(f) removing P5 of the peptide produced in step (e) to produce the side chain-protected peptide of formula

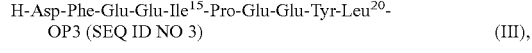

wherein P3 is as defined above,
(g) reacting the optionally side chain-protected peptide of formula II produced in step (b) with the side chain-protected peptide of formula III produced in step (f) to produce a side chain-protected peptide of formula P1-D-Phe$^1$-Pro-Arg-Pro-Gly$^5$-Gly-Gly-Gly-Asn-
Gly$^{10}$-Asp-Phe-Glu-Glu-Ile$^{15}$-Pro-Glu-Glu-Tyr-
Leu$^{20}$-OP3 (SEQ ID NO 1)          (IV), wherein P1 and P3 are as defined above, (h) removing P1, P3 and the side chain protecting groups of the peptide produced in step (g) to produce bivalirudin of formula H-D-Phe$^1$-Pro-Arg-Pro-Gly$^5$-Gly-Gly-Gly-Asn-Gly$^{10}$-
Asp-Phe-Glu-Glu-Ile$^{15}$-Pro-Glu-Glu-Tyr-Leu$^{20}$-
OH (SEQ ID NO 1)                        (I).

Here and in the following, the term "orthogonal" as characterizing attribute for the behavior of two different protecting groups, is to be understood to mean that one protecting group is cleavable by a certain method that does not affect the other protecting group. For example, "a protecting group being orthogonal to the side chain protecting groups" means a protecting group which is cleavable by a certain method that does not affect the side chain protecting groups.

The advantage of this strategy is that it can be applied on a commercial scale, thus enabling production of bivalirudin with excellent purity and in an amount of kilograms per batch without formation of nasty impurities like D-Phe$^{12}$-bivalirudin, D-Tyr$^{19}$-bivalirudin or Asp$^9$-bivalirudin. For example, when coupling the protected fragment Asp-Phe$^{12}$ to the protected peptide fragment of formula X, 5% of D-Phe$^{12}$-bivalirudin is formed, the formation of which can be unexpectedly suppressed by the process according to the invention. Catalytic hydrogenation as applied in the process according to the invention has the advantage that it is a very clean reaction method that, unlike other deprotection methods, does not induce carbocation formation, so that undesired by-products resulting from reactions between such carbocations and the target peptide are not formed. For comparison, in the route disclosed in WO 2007/033383 protection is accomplished by using tert-butyl (tBu; as tert-butyl ether or as tert-butyl ester), which is a protecting group being only cleavable by acidolysis (e.g. with hydrochloric acid or trifluoroacetic acid). This acidolysis induces the formation of by-products, such as tert-butylated tyrosine, which are difficult to remove in the final product due to their similar physicochemical properties. Another disadvantage of acidolysis is that handling large quantities of strong acids, such as trifluoroacetic acid, raises safety issues for both production and environment, especially on a commercial scale.

For further comparison, if a C-terminal protecting group which is removable by saponification, such as Et, is used as P2 for the peptides of formula VI and VII, its removal under basic condition induces substantial degradation of the asparagine residue (-Asn$^9$-) and of the arginine residue (-Arg$^3$-). Even if saponification is neither accomplished with acid nor with base but with the more gentle approach of enzymatic reaction, like saponification with the enzyme subtilisin, substantial formation of Asp$^9$-bivalirudin is observed caused by degradation of the asparagine residue.

Before, during and after the single reaction steps of the present invention, all peptide fragments as well as all coupling products may be present as such or in a suitable salt form, depending on the physicochemical properties of the molecule and/or the reaction conditions. Suitable salts are for example the salts formed with triethylamine (TEA), dicyclohexylamine (DCHA), hydrochloric acid (HCl) and trifluoroacetic acid (TFA).

In step (h), P1, P3 and the side chain protecting groups may be removed afterwards or simultaneously.

Preferably, in step (h), first P3 and the side chain protecting group(s) are removed simultaneously, and P1 is removed afterwards.

Typically, the peptide fragment obtained after each of steps (a) to (g) is isolated before subjecting to the following step. Applicant has surprisingly found that in step (h) the isolation of the peptide, obtained after simultaneous removing P3 and the side chain protecting group(s), can be dispensed with before removing P1, while obtaining similar yields and without negative effect on purity. This is surprising, as normally an isolation step is essential to remove side products which may also react in the following deprotection step and thus lower the purity of the target peptide. This finding has a positive effect on costs and time for the overall process and typically results in a higher yield of the P1-deprotected peptide as isolation usually entails loss of product. Therefore, in a more preferred embodiment of the process according to the invention, in step (h), the peptide obtained after simultaneously removing P3 and the side chain protecting group(s) is not isolated before removing P1.

Any commonly known protecting group being stable to catalytic hydrogenation may be used as P1. Suitable examples are test-butoxycarbonyl (Boc), 2-(biphenyl-4-yl) prop-2-yloxycarbonyl (Bpoc), 2-(3,5-dimethoxyphenyl) prop-2-yloxycarbonyl (Ddz), fluoren-9-ylmethoxycarbonyl (Fmoc), adamantly-1-oxycarbonyl (Adc), teramyloxycarbonyl (Aoc), diphenylphosphinyl (Dpp), 2-(methylsulfonyl) ethoxycarbonyl (Msc) and phthaloyl (Pht). Preferably, P1 is Boc, Bpoc, Ddz, Fmoc or Msc, more preferably P1 is Boc.

As protecting groups P4 and P5, any commonly known and suitable protecting group being orthogonal to the side chain protecting groups(s) and to P3 of the fragment of formula II (for P4), respectively of the amino acid of formula XIII and of the fragment of formula XIV (for P5), may be used. Preferably, P4 and P5 are stable to catalytic hydrogenation and orthogonal to the side chain protecting groups(s) and to P3. For example, suitable protecting groups are Boc, Bpoc, Ddz, Fmoc, Adc, Aoc, Dpp, Msc and Pht. Preferably, P4 and/or P5 is Boc, Bpoc, Ddz, Fmoc or Msc; more preferably P4 and/or P5 is Boc.

In a preferred embodiment of the process of the present invention, at least one of P1, P4 and P5 is Boc, Bpoc, Ddz, Fmoc or Msc; preferably at least one of P1, P4 and P5 is Boc.

As protecting group P3, any commonly known protecting group being removable by catalytic hydrogenation may be used. Suitable examples are benzyl (Bzl), benzyloxymethyl (Bom), phenacyl (Pac), 4-nitrobenzyl (ONbz), 4-pyridylmethyl (Pic), and 4-sulfobenzyl. Preferably, P3 is Bzl, Bom, Pac, ONbz, Pic or 4-sulfobenzyl with the proviso that, if P4 or P5 is Boc, Bpoc or Ddz, P3 is not Bom. More preferably P3 is Bzl. The protecting group Bom is acid sensitive and the protecting groups Boc, Bpoc and Ddz are cleavable by acid, i.e. Bom is not orthogonal to Boc, Bpoc or Dzd. This behavior excludes, here and in the following, the simultaneous use of Bom and one of the protecting groups Boc, Bpoc or Dzd.

As protecting group P2, any commonly known protecting group being removable by catalytic hydrogenation—and in case of side chain protection, concurrently being orthogonal to the side chain protecting group(s)—may be used. Suitable examples are Bzl, Bom, Pac, ONbz, Pic and 4-sulfobenzyl. Preferably, P2 is Bzl, Bom, Pac, ONbz, Pic or 4-sulfobenzyl; more preferably P2 is Bzl.

In a preferred embodiment, at least one of P2 and P3 is Bzl, Bom, Pac, ONbz, Pic or 4-sulfobenzyl, with the proviso that, if P4 or P5 is Boc, Bpoc or Ddz, P3 is not Bom. Preferably at least one of P2 and P3 is Bzl.

In a more preferred embodiment, at least one of P1, P4 and P5 is Boc, Bpoc, Ddz, Fmoc or Msc; and at least one of P2 and P3 is Bzl, Bom, Pac, ONbz, Pic, or 4-sulfobenzyl, with the proviso that, if P4 or P5 is Boc, Bpoc or Ddz, then P3 is not Bom.

Preferably, at least one of P1, P4 and P5 is Boc and at least one of P2 and P3 is Bzl.

Preferably, in the process according to the invention the side chain protected peptides/amino acids of formula III, IV, X, and XII-XIV are protected with at least one side chain protecting group selected from the group consisting of Bzl, Bom, Pac, ONbz, Pic and 4-sulfobenzyl; with the proviso that, if P4 or P5 is Boc, Bpoc or Ddz, none of the side chain protecting group is Bom.

In particular, in the process according to the invention the side chain protected peptides/amino acids of formula III, IV, X, and XII-XIV are protected with at least one Bzl as side chain protecting group(s).

Typically, the peptide of formula V is side chain-protected at the arginine residue with a suitable side chain protecting group, such as nitro, in order to avoid undesired side reactions. Typically, the peptide of formula VI is side chain-protected at the asparagine residue with a suitable side chain protecting group, especially for N-terminal protection with Fmoc, in order to avoid undesired side reactions. A suitable example is trityl (Trt), especially in case of N-terminal protection with Fmoc.

Surprisingly, applicant found that side chain protection can be dispensed with for the peptides of formula V and VI, which facilitates both their assembly and the C-terminal deprotection of their coupling product, i.e. of the peptide of formula VII. This finding allows for the disregard of orthogonality between C-terminal and side chain protection, thus making the route more straightforward. Another advantage is that the corresponding unprotected starting material is cheaper in purchase than the protected, which is important especially for production on large scale.

Preferably, in the process according to the invention, in step (a) at least one of the optionally side chain-protected peptides of formula V and VI is side chain-unprotected. In case both peptides are side chain-unprotected, the resulting peptides of formula VII and II in steps (a) and (b) are side chain-unprotected as well.

Most preferably, in the process according to the invention,
in step (a), both peptides of formula V and VI are side chain-unprotected;
in step (c), the peptide of formula X is protected with at least one side chain protecting group selected from the group consisting of Bzl, Bom, Pac, ONbz, Pic and 4-sulfobenzyl, preferably Bzl, with the proviso that, if P4 or P5 is Boc, Bpoc or Ddz, none of the side chain protecting groups is Bom; and
in step (e), the aspartic acid derivative of formula XIII is protected with a side chain protecting group selected from the group consisting of Bzl, Bom, Pac, ONbz, Pic and 4-sulfobenzyl, preferably Bzl, with the proviso that, if P4 or P5 is Boc, Bpoc or Ddz, none of the side chain protecting groups is Bom.

Even more preferably, in the process according to the invention, in step (a), both peptides of formula V and VI are side chain-unprotected; and in both of the steps (c) and (e), the at least one side chain protecting group is Bzl.

In a most preferred embodiment of the process according to the invention, in step (c) the peptide of formula X is side chain-protected with five side chain protecting groups protecting the side chains of the four glutamic acids and of tyrosine, thus affording the peptide of formula

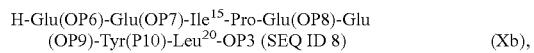

(Xb), wherein P3 is a protecting group being removable by catalytic hydrogenation, preferably P3 is Bzl, Bom, Pac, ONbz, Pic or 4-sulfobenzyl; more preferably P3 is Bzl; and each of P6 through P10 is independently selected from the group consisting of Bzl, Bom, Pac, ONbz, Pic and 4-sulfobenzyl; preferably each of P6 through P10 is Bzl; and in step (e) the side chain protected aspartic acid of formula XIII is

wherein P5 is a protecting group being orthogonal to the side chain protecting group(s) of the peptide/amino acid of formula XII and XIII and to P3; preferably P5 is stable to catalytic hydrogenation and orthogonal to the side chain protecting group(s) and to P3; more preferably P5 is Boc, Bpoc, Ddz, Fmoc or Msc; most preferably P5 is Boc; and P11 is selected from the group consisting of Bzl, Bom, Pac, ONbz, Pic and 4-sulfobenzyl; preferably P11 is Bzl.

Here and as follows, for both the C-terminus and the side chains, the abbreviation "OP[number]" indicates an ester (after reaction with a carboxylic acid both of the side chain and the C-terminus), while the abbreviation "P[number]" indicates an ether. For example, "OBzl" indicates a benzyl ester (after reaction with a carboxy group of the side chain or the C-terminus), while the abbreviation "Bzl" indicates a benzyl ether (after reaction with e.g. the phenolic hydroxy group of tyrosine).

Preferably, in the process according to the invention P1, P4 and P5 are Boc; P2, P3, P6, P7, P8, P9, P10 and P11 are Bzl;

More preferably, P1, P4 and P5 are Boc, P2, P3, P6, P7, P8, P9, P10 and P11 are Bzl and the peptides of formula V and VI are side chain-unprotected, affording a solution phase process comprising the steps of (a) reacting

 (SEQ ID NO 4)

with

 (SEQ ID NO 5)

to produce

 (SEQ ID NO 2)

(b) removing Bzl of the peptide produced in step (a) to produce

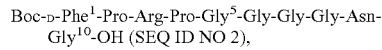

(c) reacting

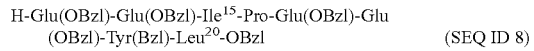 (SEQ ID 8)

with

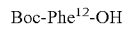

to produce

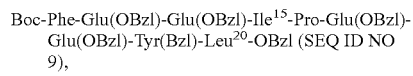

(d) removing Boc of the peptide produced in step (c) to produce the corresponding N-terminally deprotected peptide, (e) reacting the peptide produced in step (d) with Boc-Asp(OBzl)$^{11}$-OH to produce Boc-Asp(OBzl)$^{11}$-Phe-Glu(OBzl)-Glu(OBzl)-Ile$^{15}$-
   Pro-Glu(OBzl)-Glu(OBzl)-Tyr(Bzl)-Leu$^{20}$-
   OBzl (SEQ ID NO 3)

(f) removing Boc of the peptide produced in step (e) to produce

H-Asp(OBzl)$^{11}$-Phe-Glu(OBzl)-Glu(OBzl)-Ile$^{15}$-Pro-
   Glu(OBzl)-Glu(OBzl)-Tyr(Bzl)-Leu$^{20}$-OBzl (SEQ ID NO 3)

(g) reacting the peptide produced in step (b) with the peptide produced in step (f) to produce Boc-D-Phe$^{1}$-Pro-Arg-Pro-Gly$^{5}$-Gly-Gly-Gly-Asn-
   Gly$^{10}$-Asp(OBzl)-Phe-Glu(OBzl)-Glu(OBzl)-
   Ile$^{15}$-Pro-Glu(OBzl)-Glu(OBzl)-Tyr(Bzl)-Leu$^{20}$-
   OBzl (SEQ ID NO 1), and (h) removing Boc, the C-terminus-protecting Bzl and all side chain-protecting Bzl of the peptide produced in step (g) to produce bivalirudin of formula I.

This preferred embodiment is very straightforward and does not require a complicated protecting group strategy.

Preferably, in step (h), first the C-terminus-protecting Bzl and all side chain-protecting Bzl are removed simultaneously, affording N-terminally Boc-protected bivalirudin Boc-D-Phe$^{1}$-Pro-Arg-Pro-Gly$^{5}$-Gly-Gly-Gly-Asn-
   Gly$^{10}$-Asp-Phe-Glu-Glu-Ile$^{15}$-Pro-Glu-Glu-Tyr-
   Leu$^{20}$-OH (SEQ ID NO 1), and Boc is removed afterwards.

Preferably, the N-terminally Boc-protected bivalirudin obtained after simultaneous removing the C-terminus-protecting Bzl and all side chain-protecting Bzl is not isolated before removing Boc.

The C-terminal protecting groups P2, P3, as well as the side chain protecting groups P6 through P11, in case they are removable by catalytic hydrogenation, can be removed by any method of catalytic hydrogenation known to the skilled person. Hydrogenation may be accomplished by elemental hydrogen or by use of a suitable hydrogen donor like formic acid, ammonium formate, 1,3-cyclohexadiene, 1,4-cyclohexadiene or borane adducts such as tert-BuN H2.BH3. Suitable hydrogenation catalysts are for example noble metal-based hydrogenation catalysts, in particular the metals known as platinum metals, i.e. rhodium, ruthenium, palladium, osmium, iridium and platinum. Expediently, the hydrogenation catalyst is on a support such as charcoal. Depending on the activity required, the hydrogenation catalyst may be "poisoned" to lower its activity, in particular sulfided.

Optionally, suitable co-catalysts may be added to support hydrogenation. Such co-catalysts may be vanadium or molybdenum compounds like vanadium(V) oxide (V205), ammonium metavanadate (NH$_4$VO$_3$) or sodium molybdate (Na$_2$MoO$_4$).

In a preferred embodiment, the catalyst is recycled having a positive effect on both production costs and environment. For the recycling of the catalyst, any treatment suitable to recycle the catalyst may be applied.

Preferably, at least one of the removal steps (b) and (h) is carried out in a solvent with hydrogen gas and palladium on charcoal. As solvent, any inert liquid solvent which can dissolve the reactants may be used. Applicable solvents include halogenated aromatic hydrocarbons such as chlorobenzene and trifluorotoluene; halogenated hydrocarbons such as dichloromethane and dichloroethene; alcohols such as methanol, ethanol, 2-propanol, butanol and benzyl alcohol; halogenated alcohols such as 2,2,2-trifluoroethanol; carboxylic acids such as acetic acid; carboxylic esters and lactones such as ethyl acetate, methyl acetate and valerolactone; and organic solvents containing heteroatoms such as N-methylpyrrolidone (NMP) or N,N-dimethylformamide (DMF). The solvents can be used alone, as solvent mixture or as mixture with water. Depending on the solubility of the peptide fragment, even neat water may be used. Therefore, in step (b) removal may be accomplished in neat water as solvent.

A preferred solvent is selected from the group consisting of DMF, acetone, acetic acid, a mixture of acetone and water, and a mixture of acetic acid and water.

In a preferred embodiment, the removal step (b) is carried out in a solvent selected from the group consisting of DMF, acetone, water, and a mixture of acetone and water; particularly in DMF.

More preferably, the removal step (b) is carried out in DMF. Surprisingly, it was found out that the solvent used in removal step (b) has an influence on the impurity profile of final bivalirudin. It was observed that DMF is advantageous compared to e.g. a mixture of acetone and water so that the impurity formed after double incorporation of -D-Phe$^{1}$-Pro-Arg-Pro-Gly$^{5}$-Gly-Gly-Gly-Asn-Gly$^{10}$- (SEQ ID NO 2) can be suppressed.

In another preferred embodiment, the removal step (h) is carried out in acetic acid or a mixture of acetic acid and water; particularly in a mixture of acetic acid and water.

The hydrogenation processes of the removal steps (b) and (h) may be carried out at atmospheric pressure or superatmospheric pressure. Typical pressures are from 1 to 100 bar. Advantageously, 1 to 70 bar; in particular 2 to 10 bar are used.

The hydrogenation reactions of the removal steps (b) and (h) may be carried out at low or elevated temperatures. An examplary temperature range is from −20° C. to 70° C. Preferred is a temperature between 0° C. and 60° C., and most preferred is a range from 10° C. to 40° C.

The coupling steps (a), (c), (e) and (g) of the process according to the invention are performed in solution phase and can be carried out using reaction conditions known in the art of peptide synthesis. Coupling of the respective side chain-unprotected or protected peptide fragments/amino acid derivatives can be accomplished using in situ coupling reagents, for example phoshonium or uronium coupling reagents, like benzotriazol-1-yloxy-tris(dimethylamino) phosphonium hexafluorophosphate (BOP), benzotriazol-1-yloxy-tris(pyrrolidino)phosphonium hexafluorophosphate (PyBOP), O-(benzotriazol-1-yl)-1,1,3,3-tetramethyluronium hexafluorophosphate (HBTU), O-(6-chlorobenzotriazol-1-yl)-1,1,3,3-tetramethyluronium hexafluorophosphate (HCTU), O-(6-chlorobenzotriazol-1-yl)-1,1,3,3-tetramethyluronium tetrafluoroborate (TCTU), O-(7-azabenzotriazol-1-yl)-1,1,3,3-tetramethyluronium hexafluorophosphate (HATU), O-(7-azabenzotriazol-1-yl)-1,1,3,3-tetramethyluronium tetrafluoroborate (TATU), O-(benzotriazol-1-yl)-1,1,3,3-tetramethyluronium tetrafluoroborate (TBTU), and O-[cyano(ethoxycarbonyl)methylenamino]-1,1,3,3-tetramethyluronium tetrafluoroborate (TOTU), or carbodiimide coupling reagents, like diisopropylcarbodiimide (DIC), dicyclohexylcarbodiimide (DCC) and water-soluble carbodiimides (WSCDI) like 1-ethyl-3-(3-dimethylaminopropyl)carbodiimide (EDC) optionally as salt like as hydrochloride salt. Other coupling techniques use pre-formed active esters, such as N-hydroxysuccinimide (HOSu) and p-nitrophenol (HONp) esters, pre-formed symmetrical anhydrides, non-symmetrical anhydrides such as N-carboxyanhydrides (NCAs) and acid halides, such as acyl fluorides or acyl chlorides. Preferred coupling reagents are carbodiimide coupling reagents, most preferred are DIC or EDC, suitably as EDC salt such as EDC.HCl.

The reaction mixture of the coupling steps (a), (c), (e) and (g) may advantageously contain a base, preferably a tertiary amine base, which both deprotonates the carboxy component and neutralizes the counterion of the amino component, and thus facilitates the in situ reaction. Suitable bases are for example trialkylamines, like N,N-diisopropylethylamine (DIPEA) or triethylamine (TEA); N,N-dialkylanilines, like N,N-diethylaniline; 2,4,6-trialkylpyridines, like 2,4,6-trimethylpyridine; and N-alkylmorpholines, like N-methylmorpholine. In particular, the reaction mixture advantageously contains TEA or DIPEA as a base.

The reaction mixture of the coupling steps (a), (c), (e) and (g) can additionally contain auxiliary nucleophiles as additives due their positive effect in suppressing undesired side reactions. Any known auxiliary nucleophile may be applied. Examples of suitable auxiliary nucleophiles are 1-hydroxybenzotriazole (HOBt), N-hydroxysuccinimide (HOSu), N-hydroxy-3,4-dihydro-4-oxo-1,2,3-benzotriazine (HOOBt) and 1-hydroxy-7-azabenzotriazole (HOAt). Preferably, the reaction mixtures of the coupling steps additionally contain HOBt.

In a preferred embodiment, the coupling mixture of the coupling steps (a), (c), (e) and (g) is selected from the group consisting of DIC/HOBt/TEA, EDC/HOBt/DIPEA and EDC/HOBt/TEA.

As solvent of the coupling steps (a), (c), (e) and (g), any inert liquid solvent which can dissolve the reactants may be used. Applicable coupling solvents are water-miscible solvents like dimethyl sulfoxide (DMSO), dioxane, tetrahydrofuran (THF), 1-methyl-2-pyrrolidone (NMP), N,N-dimethylformamide (DMF), N,N-dimethylacetamide (DMA), or any mixture thereof; non water-miscible solvents like dichloromethane (DCM), ethyl acetate or any mixture thereof; and any suitable mixture between water-miscible and non water-miscible solvents, including mixtures with water. A preferred solvent is DMF or a mixture of DMF and water.

N-terminal deprotection of the steps (d), (f) and (h) can be carried out using reaction conditions known in the art of peptide synthesis and depends on the nature of the protecting groups P1, P4 and P5. In case the protecting group is Boc, deprotection is suitably accomplished by acid, preferably by trifluoroacetic acid, which may be applied neat or as a mixture with an inert solvent, like toluene, THF or a mixture of toluene and THF. In case the protecting group is Fmoc, Akerminal deprotection can be achieved by reaction with a base, favorably with a secondary amine such as piperidine or diethylamine. Typically, N-terminal deprotection is carried out in a solvent which can be any solvent which does not interfere with the reactants like chlorinated hydrocarbons such as dichloromethane; alkylated amides and lactames such as dimethylformamide or 1-methyl-2-pyrrolidone; aromatic hydrocarbons such as toluene; ethers such as THF or any mixture thereof. Preferably, deprotection of the N-terminal Boc group is carried out in toluene or in a mixture of phenol, toluene and THF.

The crude bivalirudin obtained after step (h) may be purified by conventional methods, like preparative HPLC or countercurrent distribution. Purifications steps may be repeated.

The same applies to the peptide fragments obtained after steps (a) to (g).

The final bivalirudin of formula I can be isolated according to known isolation methods in peptide chemistry, such as precipitation or freeze-drying which is also known as lyophilization.

The optionally side chain-protected peptides of formula V and VI and the side chain-protected peptide of formula X can be prepared using conventional peptide synthesis methods, e.g. solution phase synthesis (synonym: homogeneous phase peptide synthesis, abbreviated as HPPS), solid phase peptide synthesis (SPPS) or a combination of SPPS and HPPS called mixed synthesis (synonym: mixed phase peptide synthesis, abbreviated as MPPS).

In an embodiment of the process according to the present invention, at least one of the peptides selected from the group consisting of the optionally side chain-protected peptide of formula V, the optionally side chain-protected peptide of formula VI and the side chain-protected peptide of formula X is prepared by solution phase synthesis in a preceding process. Preferably, these peptides are assembled starting with the corresponding dipeptides, i.e. the sequence patterns -D-Phe$^1$-Pro-, -Arg$^3$-Pro-, -Gly$^5$-Gly-, -Asn$^9$-Gly-, -Glu$^{13}$-Glu-, -Ile$^{15}$-Pro-, -Glu$^{17}$-Glu- or -Tyr$^{19}$-Leu-. The N-terminal, C-terminal and side chain protecting groups as well as the reaction conditions may be any as known to the skilled person, preferably be the same or similar as described above.

In particular, the process for the production of the optionally side chain-protected peptide of formula $$P1\text{-}\text{D-Phe}^1\text{-Pro-Arg-Pro-OH (SEQ ID NO 4)} \quad\quad (V),$$

preferably of the side chain-unprotected peptide Va,
wherein
P1 is a protecting group, preferably P1 is a protecting group being stable to catalytic hydrogenation, more preferably P1 is Boc, Bpoc, Ddz, Fmoc or Msc, most preferably P1 is Boc;
in solution phase, comprises the steps of
(a) removing P12 of an optionally side chain-protected dipeptide of formula $$P12\text{-Arg-Pro}^4\text{-OP13} \quad\quad (XVI),$$

preferably of the side chain-unprotected dipeptide XVIa,
wherein
P12 is a protecting group, preferably P12 is a protecting group being orthogonal to the side chain protecting group(s) and to P13, more preferably P12 is a protecting group being stable to catalytic hydrogenation and orthogonal to the side chain protecting group(s) and to P13, even more preferably P12 is Boc, Bpoc, Ddz, Fmoc or Msc, most preferably P12 is Boc; and
P13 is a protecting group such as Bzl, methyl (Me) or ethyl (Et); preferably P13 is a protecting group being removable by catalytic hydrogenation and orthogonal to the side chain protecting group(s), more preferably P13 is Bzl, Bom, Pac, ONbz, Pic, or 4-sulfobenzyl, most preferably P13 is Bzl;
with the proviso that, if P12 is Boc, Bpoc, Ddz, then P13 is not Bom;
(b) reacting the N-terminally deprotected, optionally side chain-protected dipeptide, preferably the corresponding side chain-unprotected dipeptide, produced in step (a) with an optionally side chain-protected dipeptide of formula $$P1\text{-}\text{D-Phe}^1\text{-Pro-OW} \quad\quad (XVII),$$

preferably with the side chain-unprotected dipeptide XVIIa, wherein
P1 is as defined above, and W is hydrogen or a pre-activation group such as pentafluorophenyl (Pfp),
to produce an optionally side chain-protected peptide of formula P1-D-Phe$^1$-Pro-Arg-Pro-OP13 (SEQ ID NO 4)   (XV), preferably the side chain-unprotected peptide XVa,
wherein
P1 and P13 are as defined above, and
(c) removing P13 of the optionally side chain-protected peptide of formula XV, preferably of the side chain-unprotected peptide XVa, produced in step (b) to produce the optionally side chain-protected peptide of formula V; preferably the side chain-unprotected peptide Va.

Also in particular, the process for the production of the optionally side chain-protected peptide of formula H-Gly$^5$-Gly-Gly-Gly-Asn-Gly$^{10}$-OP2 (SEQ ID NO 5)   (VI), preferably of the side chain-unprotected peptide VIa,
wherein
P2 is a protecting group, preferably P2 is a protecting group being removable by catalytic hydrogenation and being orthogonal to the optional side chain protecting group(s), more preferably P2 is Bzl, Bom, Pac, ONbz, Pic, or 4-sulfobenzyl, most preferably P2 is Bzl,
in solution phase, comprises the steps of
(a) removing P14 of an optionally side chain-protected dipeptide of formula P14-Asn-Gly$^{10}$-OP2   (XVIII), preferably of the side chain-unprotected dipeptide XVIIIa,
wherein
P14 is a protecting group, preferably P14 is a protecting group being orthogonal to the side chain protecting group(s) and to P2, more preferably P14 is a protecting group being stable to catalytic hydrogenation and orthogonal to the side chain protecting group(s) and to P2, even more preferably P14 is Boc, Bpoc, Ddz, Fmoc or Msc, most preferably P14 is Boc; and
P2 is as defined above;
with the proviso that, if P14 is Boc, Bpoc or Ddz, then P2 is not Bom;
(b) reacting the N-terminally deprotected, optionally side chain-protected dipeptide, preferably the side chain-unprotected dipeptide, produced in step (a) with tetraglycine of formula P15-Gly$^5$-Gly-Gly-Gly-OH (SEQ ID NO 10)   (IXX), wherein
P15 is a protecting group, preferably P15 is a protecting group being orthogonal to the side chain protecting group of the peptide of formula XX, more preferably P15 is a protecting group being stable to catalytic hydrogenation and orthogonal to the side chain protecting group of the peptide of formula XX, even more preferably P15 is Boc, Bpoc, Ddz, Fmoc or Msc, most preferably P15 is Boc; to produce an optionally side chain-protected peptide of formula P15-Gly$^5$-Gly-Gly-Gly-Asn-Gly$^{10}$-OP2 (SEQ ID NO 5)   (XX), preferably the side chain-unprotected peptide XXa,
wherein
P2 and P15 are as defined above,
with the proviso that, if P15 is Boc, Bpoc or Ddz, then P2 is not Bom and (c) removing P15 of the optionally side chain-protected peptide of formula XX, preferably of the side chain-unprotected peptide XXa, produced in step (b) to produce the optionally side chain-protected peptide of formula VI; preferably the side chain-unprotected peptide VIa.

Further in particular, the process for the production of the side chain-protected peptide of formula H-Glu-Glu-Ile$^{15}$-Pro-Glu-Glu-Tyr-Leu$^{20}$-OP3 (SEQ ID NO 8)   (X), preferably of the peptide of formula H-Glu(OP6)-Glu(OP7)-Ile$^{15}$-Pro-Glu(OP8)-Glu(OP9)-Tyr(P10)-Leu$^{20}$-OP3 (SEQ ID 8)   (Xb), wherein
P3 is a protecting group, preferably P3 is a protecting group being removable by catalytic hydrogenation, more preferably P3 is Bzl, Bom, Pac, ONbz, Pic or 4-sulfobenzyl, most preferably P3 is Bzl, and
each of P6 through P10 is independently selected from the group consisting of Bzl, Bom, Pac, ONbz, Pic and 4-sulfobenzyl, preferably each of P6 through P10 is Bzl, in solution phase, comprises the steps of
(a) removing P16 of a side chain-protected peptide of formula P16-Glu-Glu-Ty-Leu$^{20}$-OP3 (SEQ ID NO 6)   (VIII), preferably of the peptide of formula P16-Glu(OP8)-Glu(OP9)-Tyr(P10)-Leu$^{20}$-OP3 (SEQ ID NO 6)   (VIIIb), wherein
P3 and P8 through P10 are as defined above, and
P16 is a protecting group, preferably P16 is a protecting group being orthogonal to the side chain protecting group(s) and to P3, more preferably P16 is a protecting group being stable to catalytic hydrogenation and orthogonal to the side chain protecting group(s) and to P3, even more preferably P16 is Boc, Bpoc, Ddz, Fmoc or Msc, most preferably P16 is Boc;
with the proviso that, if P16 is Boc, Bpoc or Ddz, then P3 is not Bom;
(b) reacting the N-terminally deprotected, side chain-protected peptide of formula VIII, preferably the corresponding peptide VIIIb, produced in step (a) with a side chain-protected peptide of formula P17-Glu-Glu-Ile$^{15}$-Pro-OH (SEQ ID NO 7)   (IX), preferably of P17-Glu(OP6)-Glu(OP7)-Ile$^{15}$-Pro-OH (SEQ ID NO 7)   (IXb), wherein
P6 and P7 are as defined above, and
P17 is a protecting group, preferably P17 is a protecting group being orthogonal to the side chain protecting group(s), more preferably P17 is a protecting group being stable to catalytic hydrogenation and orthogonal to the side chain protecting group(s), even more preferably P17 is Boc, Bpoc, Ddz, Fmoc or Msc, most preferably P17 is Boc,
to produce a side chain-protected peptide of formula P17-Glu-Glu-Ile$^{15}$-Pro-Glu-Glu-Tyr-Leu$^{20}$-OP3 (SEQ ID NO 8)   (XXI), preferably of the peptide of formula P17-Glu(OP6)-Glu(OP7)-Ile$^{15}$-Pro-Glu(OP8)-Glu(OP9)-Tyr(P10)-Leu$^{20}$-OP3 (SEQ ID 8)   (XXIb), wherein
P3, P6 through P10 and P17 are as defined above
with the proviso that, if P17 is Boc, Bpoc or Ddz, then P3 or any one of P6 through P10 is not Bom, and
(c) removing P17 of the side chain-protected peptide of formula XXI, preferably of the corresponding peptide XXIb, produced in step (b) to produce the side chain-protected peptide of formula X; preferably the peptide Xb.

In a further embodiment of the process according to the present invention, at least one of the peptides selected from the group consisting of the optionally side chain-protected peptide of formula V, the optionally side chain-protected peptide of formula VI and the side chain-protected peptide of formula X is prepared by solid phase synthesis in a preceding process. Thereby, any commonly known SPPS method, including SPPS building blocks and SPPS conditions, may be employed. All resins being known to the person skilled in the art and allowing the preparation of protected peptides can be applied. Here, resins are to be interpreted in a wide manner. Therefore, the term "resin" is to be understood to mean e.g. a solid support alone or a solid support directly linked to a linker, optionally with a handle in between. The resin may be insoluble or soluble. The soluble polymer polyethylene glycol (soluble PEG polymer) is an example for the solid support of a soluble resin thus forming a soluble peptide-resin after assembly of the single building blocks. Preferred resins are polystyrene-based resins with trityl or bromobenzhydryl. Examples for trityl resins are 2-chlorotrityl chloride resin (CTC resin), trityl chloride resin, 4-methyltrityl chloride resin and 4-methoxytrityl chloride resin. Preferably, the CTC resin is applied for the synthesis of said peptide fragments.

Another object of the present invention is to provide peptides which are useful as intermediates in the process of the invention. In particular, one of these peptides is a peptide selected from the group consisting of (i) an optionally side chain-protected peptide of formula

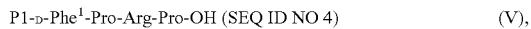

P1-D-Phe$^1$-Pro-Arg-Pro-OH (SEQ ID NO 4)　　　(V), wherein P1 is a protecting group, preferably P1 is a protecting group being stable to catalytic hydrogenation, more preferably P1 is Boc, Bpoc, Ddz, Fmoc or Msc, most preferably P1 is Boc; and
said peptide is optionally side chain-protected at the arginine residue with a suitable side chain protecting group such as nitro;

(ii) an optionally side chain-protected peptide of formula

H-Gly$^5$-Gly-Gly-Gly-Asn-Gly$^{10}$-OP2 (SEQ ID NO 5)　　　(VI), wherein P2 is a protecting group, preferably P2 is a protecting group being removable by catalytic hydrogenation and being orthogonal to the optional side chain protecting group(s), more preferably P2 is Bzl, Bom, Pac, ONbz, Pic, or 4-sulfobenzyl, most preferably P2 is Bzl; and
said peptide is optionally side chain-protected at the asparagine residue with a suitable side chain protecting group such as trityl (Trt);

(iii) an optionally side chain-protected peptide of formula

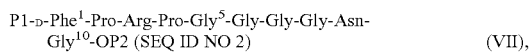

P1-D-Phe$^1$-Pro-Arg-Pro-Gly$^5$-Gly-Gly-Gly-Asn-Gly$^{10}$-OP2 (SEQ ID NO 2)　　　(VII), wherein P1, P2 and the optional side chain protecting group(s), as well as the preferred meanings of P1, of P2 and of the optional side chain protecting group(s), are as defined above;

(iv) a side chain-protected peptide of formula

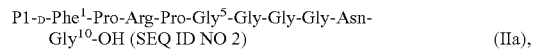

P1-D-Phe$^1$-Pro-Arg-Pro-Gly$^5$-Gly-Gly-Gly-Asn-Gly$^{10}$-OH (SEQ ID NO 2)　　　(IIa), wherein P1 and the side chain protecting group(s), as well as the preferred meanings of P1 and of the optional side chain protecting group(s), are as defined above,
except for Boc-D-Phe$^1$-Pro-Arg(Pbf)-Pro-Gly$^5$-Gly-Gly-Gly-Asn(Trt)-Gly$^{10}$-OH (SEQ ID NO 2) with Pbf being pentamethyldihydrobenzofuransulfonyl and Trt being trityl. This peptide is disclosed in WO 2007/033383 as the product of a solid phase synthesis on CTC resin. In contrast, the side chain-protected peptide of formula IIa according to the present invention is formed by a different way, namely by solution phase synthesis;

(v) a side chain-unprotected peptide of formula

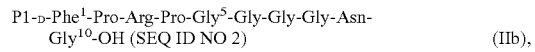

P1-D-Phe$^1$-Pro-Arg-Pro-Gly$^5$-Gly-Gly-Gly-Asn-Gly$^{10}$-OH (SEQ ID NO 2)　　　(IIb), wherein P1, as well as the preferred meanings of P1, are as defined above;

(vi) a side chain-protected peptide of formula

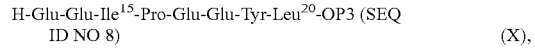

H-Glu-Glu-Ile$^{15}$-Pro-Glu-Glu-Tyr-Leu$^{20}$-OP3 (SEQ ID NO 8)　　　(X), wherein P3 is a protecting group, preferably P3 is a protecting group being removable by catalytic hydrogenation, more preferably P3 is Bzl, Bom, Pac, ONbz, Pic, or 4-sulfobenzyl, most preferably P3 is Bzl; and
the side chain protecting group(s) is/are at least one suitable side chain protecting group(s), preferably selected from the group consisting of Bzl, Bom, Pac, ONbz, Pic, and 4-sulfobenzyl, more preferably Bzl;

(vii) a side chain-protected peptide of formula

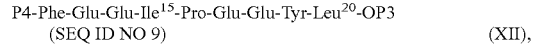

P4-Phe-Glu-Glu-Ile$^{15}$-Pro-Glu-Glu-Tyr-Leu$^{20}$-OP3 (SEQ ID NO 9)　　　(XII), wherein P3 and the side chain protecting group(s), as well as the preferred meanings of P3 and of the optional side chain protecting group(s), are as defined above; and
P4 is a protecting group, preferably P4 is a protecting group being orthogonal to the side chain protecting group(s) of the peptide of formula X and to P3, more preferably P4 is Boc, Bpoc, Ddz, Fmoc or Msc, most preferably P4 is Boc, with the proviso that, if P4 is Boc, Bpoc or Ddz, then P3 is not Bom;
or
P4 is hydrogen;

(viii) a side chain-protected peptide of formula

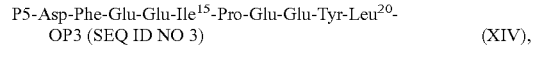

P5-Asp-Phe-Glu-Glu-Ile$^{15}$-Pro-Glu-Glu-Tyr-Leu$^{20}$-OP3 (SEQ ID NO 3)　　　(XIV), wherein P3 and the side chain protecting group(s), as well as the preferred meanings of P3 and of the side chain protecting group(s), are as defined above; and
P5 is a protecting group, preferably P5 is a protecting group being orthogonal to the side chain protecting group(s) of the peptide/amino acid of formula XII and XIII and to P3, more preferably P5 is Boc, Bpoc, Ddz, Fmoc or Msc, most preferably P5 is Boc, with the proviso that, if P5 is Boc, Bpoc or Ddz, then P3 is not Bom,
except for Fmoc-Asp(OtBu)-Phe-Glu(OtBu)-Glu(OtBu)-Ile$^{15}$-Pro-Glu(OtBu)-Glu(OtBu)-Tyr(tBu)-Leu$^{20}$-OtBu (SEQ ID NO 3) with tBu being tert-butyl. This peptide is disclosed in WO 2007/033383 as the product of the reaction between a precursor peptide (i.e. peptide sequence minus Leu) and H-Leu-OtBu. The precursor peptide as disclosed in WO 2007/033383 has been formed in a preceding step by solid phase synthesis on CTC resin. After reaction with H-Leu-OtBu, the disclosed peptide is not isolated before continuing with the next step. In contrast, the side chain-protected peptide of formula XIV according to the present invention is formed by a different way, namely by solution phase synthesis, and it is isolated after its formation;

(ix) a side chain-protected peptide of formula $$\text{H-Asp-Phe-Glu-Glu-Ile}^{15}\text{-Pro-Glu-Glu-Tyr-Leu}^{20}\text{-OP3 (SEQ ID NO 3)} \quad \text{(III)},$$

wherein P3 and the side chain protecting group(s), as well as the preferred meanings of P3 and of the side chain protecting group(s), are as defined above, except for H-Asp(OtBu)-Phe-Glu(OtBu)-Glu(OtBu)-Ile$^{15}$-Pro-Glu(OtBu)-Glu(OtBu)-Tyr(tBu)-Leu$^{20}$-OtBu (SEQ ID NO 3). This peptide is disclosed in WO 2007/033383. It is the N-terminally deprotected peptide described above. Accordingly, as explained above, its way of formation is different from the side chain-protected peptide of formula III according to the present invention; and (x) a side chain-protected peptide of formula $$\text{P1-d-Phe}^1\text{-Pro-Arg-Pro-Gly}^5\text{-Gly-Gly-Gly-Asn-Gly}^{10}\text{-Asp-Phe-Glu-Glu-Ile}^{15}\text{-Pro-Glu-Glu-Tyr-Leu}^{20}\text{-OP3 (SEQ ID NO 1)} \quad \text{(IV)},$$

wherein P1, P3 and the side chain protecting group(s), as well as the preferred meanings of P1, of P3 and of the optional side chain protecting group(s), are as defined above, except for Boc-d-Phe$^1$-Pro-Arg(Pbf)-Pro-Gly$^5$-Gly-Gly-Gly-Asn(Trt)-Gly$^{10}$-Asp(OtBu)-Phe-Glu(OtBu)-Glu(OtBu)-Ile$^{15}$-Pro-Glu(OtBu)-Glu(OtBu)-Tyr(tBu)-Leu$^{20}$-OtBu (SEQ ID NO 1). This peptide is disclosed in WO 2007/033383 as product after coupling Boc-d-Phe$^1$-Pro-Arg(Pbf)-Pro-Gly$^5$-Gly-Gly-Gly-Asn(Trt)-Gly$^{10}$-OH and H-Asp(OtBu)-Phe-Glu(OtBu)-Glu(OtBu)-Ile$^{15}$-Pro-Glu(OtBu)-Glu(OtBu)-Tyr(tBu)-Leu$^{20}$-OtBu, both of which are explained above. Accordingly, the way towards its coupling product is different from the way toward the side chain-protected peptide of formula IV according to the present invention.

In a preferred embodiment, the peptide of formula V is side chain-unprotected and is of formula Boc-d-Phe$^1$-Pro-Arg-Pro-OH (SEQ ID NO 4), which comprises the sequence of amino acid position 1-4 of bivalirudin.

In another preferred embodiment, the peptide of formula VI is side chain-unprotected and is of formula H-Gly$^5$-Gly-Gly-Gly-Asn-Gly$^{10}$-OBzl (SEQ ID NO 5), which comprises the sequence of amino acid position 5-10 of bivalirudin.

In another preferred embodiment, the peptide of formula VII is side chain-unprotected and is of formula Boc-d-Phe$^1$-Pro-Arg-Pro-Gly$^5$-Gly-Gly-Gly-Asn-Gly$^{10}$-OBzl (SEQ ID NO 2), which comprises the sequence of amino acid position 1-10 of bivalirudin.

In another preferred embodiment, the side chain-unprotected peptide of formula IIb is Boc-d-Phe$^1$-Pro-Arg-Pro-Gly$^5$-Gly-Gly-Gly-Asn-Gly$^{10}$-OH (SEQ ID NO 2), which comprises the sequence of amino acid position 1-10 of bivalirudin.

In another preferred embodiment, the side chain-protected peptide of formula X is H-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 8), which comprises the sequence of amino acid position 13-20 of bivalirudin.

In another preferred embodiment, the side chain-protected peptide of formula XII is Boc-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 9), or H-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 9), which both comprise the sequence of amino acid position 12-20 of bivalirudin.

In another preferred embodiment, the side chain-protected peptide of formula XIV is Boc-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 3), which comprises the sequence of amino acid position 11-20 of bivalirudin.

In another preferred embodiment, the side chain-protected peptide of formula III is H-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 3), which comprises the sequence of amino acid position 11-20 of bivalirudin.

In another preferred embodiment, the side chain-protected peptide of formula IV is Boc-d-Phe$^1$-Pro-Arg-Pro-Gly$^5$-Gly-Gly-Gly-Asn-Gly$^{10}$-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 1), which comprises the sequence of amino acid position 1-20 of bivalirudin.

In another aspect, the present invention relates to the use of a peptide selected from the group consisting of (i) an optionally side chain-protected peptide of formula P1-d-Phe$^1$-Pro-Arg-Pro-OH (SEQ ID NO 4)   (V), wherein P1 is a protecting group, preferably P1 is a protecting group being stable to catalytic hydrogenation, more preferably P1 is Boc, Bpoc, Ddz, Fmoc or Msc, most preferably P1 is Boc; and said peptide is optionally side chain-protected at the arginine residue with a suitable side chain protecting group such as nitro;

preferably, the peptide V is side chain-unprotected and is of formula

Boc-d-Phe$^1$-Pro-Arg-Pro-OH (SEQ ID NO 4);

(ii) an optionally side chain-protected peptide of formula

H-Gly$^5$-Gly-Gly-Gly-Asn-Gly$^{10}$-OP2 (SEQ ID NO 5)   (VI), wherein P2 is a protecting group, preferably P2 is a protecting group being removable by catalytic hydrogenation and being orthogonal to the optional side chain protecting group(s), more preferably P2 is Bzl, Bom, Pac, ONbz, Pic, or 4-sulfobenzyl, most preferably P2 is Bzl; and said peptide is optionally side chain-protected at the asparagine residue with a suitable side chain protecting group such as trityl (Trt);
preferably, the peptide VI is side chain-unprotected and is of formula H-Gly$^5$-Gly-Gly-Gly-Asn-Gly$^{10}$-OBzl (SEQ ID NO 5);

(iii) an optionally side chain-protected peptide of formula

P1-D-Phe$^1$-Pro-Arg-Pro-Gly$^5$-Gly-Gly-Gly-Asn-Gly$^{10}$-OP2 (SEQ ID NO 2)        (VII), wherein P1, P2 and the optional side chain protecting group(s), as well as the preferred meanings of P1, of P2 and of the optional side chain protecting group(s), are as defined above;
preferably, the peptide VII is side chain-unprotected and is of formula Boc-D-Phe$^1$-Pro-Arg-Pro-Gly$^5$-Gly-Gly-Gly-Asn-Gly$^{10}$-OBzl (SEQ ID NO 2);

(iv) a side chain-protected peptide of formula

P1-D-Phe$^1$-Pro-Arg-Pro-Gly$^5$-Gly-Gly-Gly-Asn-Gly$^{10}$-OH (SEQ ID NO 2)        (IIa), wherein P1 and the side chain protecting group(s), as well as the preferred meanings of P1 and of the optional side chain protecting group(s), are as defined above,
except for Boc-D-Phe$^1$-Pro-Arg(Pbf)-Pro-Gly$^5$-Gly-Gly-Gly-Asn(Trt)-Gly$^{10}$-OH (SEQ ID NO 2) with Pbf being pentamethyldihydrobenzofuransulfonyl and Trt being trityl. This peptide is disclosed in WO 2007/033383 as the product of a solid phase synthesis on CTC resin. In contrast, the side chain-protected peptide of formula IIa according to the present invention is formed by a different way, namely by solution phase synthesis;
(v) a side chain-unprotected peptide of formula P1-D-Phe$^1$-Pro-Arg-Pro-Gly$^5$-Gly-Gly-Gly-Asn-Gly$^{10}$-OH (SEQ ID NO 2)        (IIb), wherein P1, as well as the preferred meanings of P1, are as defined above;
preferably, the side chain-unprotected peptide of formula IIb is Boc-D-Phe$^1$-Pro-Arg-Pro-Gly$^5$-Gly-Gly-Gly-Asn-Gly$^{10}$-OH (SEQ ID NO 2);

(vi) a side chain-protected peptide of formula

H-Glu-Glu-Ile$^{15}$-Pro-Glu-Glu-Tyr-Leu$^{20}$-OP3 (SEQ ID NO 8)        (X), wherein P3 is a protecting group, preferably P3 is a protecting group being removable by catalytic hydrogenation, more preferably P3 is Bzl, Bom, Pac, ONbz, Pic, or 4-sulfobenzyl, most preferably P3 is Bzl; and
the side chain protecting group(s) is/are preferably selected from the group consisting of Bzl, Bom, Pac, ONbz, Pic, and 4-sulfobenzyl, more preferably Bzl;
preferably, the side chain-protected peptide of formula X is H-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 8);

(vii) a side chain-protected peptide of formula

P4-Phe-Glu-Glu-Ile$^{15}$-Pro-Glu-Glu-Tyr-Leu$^{20}$-OP3 (SEQ ID NO 9)        (XII), wherein P3 and the side chain protecting group(s), as well as the preferred meanings of P3 and of the optional side chain protecting group(s), are as defined above; and P4 is a protecting group, preferably P4 is a protecting group being orthogonal to the side chain protecting group(s) of the peptide of formula X and to P3, more preferably P4 is Boc, Bpoc, Ddz, Fmoc or Msc, most preferably P4 is Boc, with the proviso that, if P4 is Boc, Bpoc or Ddz, then P3 is not Bom;
or
P4 is hydrogen;
preferably, the side chain-protected peptide of formula XII is Boc-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 9), or H-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 9);

(viii) a side chain-protected peptide of formula

P5-Asp-Phe-Glu-Glu-Ile$^{15}$-Pro-Glu-Glu-Tyr-Leu$^{20}$-OP3 (SEQ ID NO 3)        (XIV), wherein P3 and the side chain protecting group(s), as well as the preferred meanings of P3 and of the side chain protecting group(s), are as defined above; and
P5 is a protecting group, preferably P5 is a protecting group being orthogonal to the side chain protecting group(s) of the peptide/amino acid of formula XII and XIII and to P3, more preferably P5 is Boc, Bpoc, Ddz, Fmoc or Msc, most preferably P5 is Boc, with the proviso that, if P5 is Boc, Bpoc or Ddz, then P3 is not Bom,
Except for Fmoc-Asp(OtBu)-Phe-Glu(OtBu)-Glu(OtBu)-Ile$^{15}$-Pro-Glu(OtBu)-Glu(OtBu)-Tyr(tBu)-Leu$^{20}$-OtBu (SEQ ID NO 3), with tBu being terbutyl. This peptide is disclosed in WO 2007/033383 as the product of the reaction between a precursor peptide (i.e. peptide sequence minus Leu) and H-Leu-OtBu. The precursor peptide as disclosed in WO 2007/033383 has been formed in a preceding step by solid phase synthesis on CTC resin. After reaction with H-Leu-OtBu, the disclosed peptide is not isolated before continuing with the next step. In contrast, the side chain-protected peptide of formula XIV according to the present invention is formed by a different way, namely by solution phase synthesis, and it is isolated after its formation;
preferably, the side chain-protected peptide of formula XIV is Boc-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 3);

(ix) a side chain-protected peptide of formula

H-Asp-Phe-Glu-Glu-Ile$^{15}$-Pro-Glu-Glu-Tyr-Leu$^{20}$-OP3 (SEQ ID NO 3)        (III), wherein P3 and the side chain protecting group(s), as well as the preferred meanings of P3 and of the side chain protecting group(s), are as defined above, except for H-Asp(OtBu)-Phe-Glu(OtBu)-Glu(OtBu)-Ile$^{15}$-Pro-Glu(OtBu)-Glu(OtBu)-Tyr(tBu)-Leu$^{20}$-OtBu (SEQ ID NO 3). This peptide is disclosed in WO 2007/033383. It is the N-terminally deprotected peptide described above. Accordingly, as explained above, its way of formation is different from the side chain-protected peptide of formula III according to the present invention;

preferably, the side chain-protected peptide of formula III is

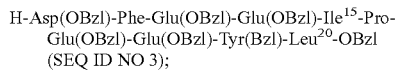
H-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 3);

and (x) a side chain-protected peptide of formula

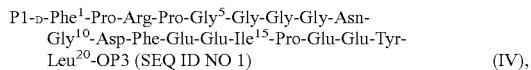
P1-D-Phe$^1$-Pro-Arg-Pro-Gly$^5$-Gly-Gly-Gly-Asn-Gly$^{10}$-Asp-Phe-Glu-Glu-Ile$^{15}$-Pro-Glu-Glu-Tyr-Leu$^{20}$-OP3 (SEQ ID NO 1)   (IV), wherein P1, P3 and the side chain protecting group(s), as well as the preferred meanings of P1, of P3 and of the optional side chain protecting group(s), are as defined above,
except for Boc-D-Phe$^1$-Pro-Arg(Pbf)-Pro-Gly$^5$-Gly-Gly-Gly-Asn(Trt)-Gly$^{10}$-Asp(OtBu)-Phe-Glu(OtBu)-Glu(OtBu)-Ile$^{15}$-Pro-Glu(OtBu)-Glu(OtBu)-Tyr(tBu)-Leu$^{20}$-OtBu (SEQ ID NO 1). This peptide is disclosed in WO 2007/033383 as product after coupling sequence "Boc-D-Phe$^1$-Pro-Arg(Pbf)-Pro-Gly$^5$-Gly-Gly-Gly-Asn(Trt)-Gly$^{10}$-OH (SEQ ID NO 2)". and H-Asp(OtBu)-Phe-Glu(OtBu)-Glu(OtBu)-Ile$^{15}$-Pro-Glu(OtBu)-Glu(OtBu)-Tyr(tBu)-Leu$^{20}$-OtBu (SEQ ID NO 3), both of which are explained above. Accordingly, the way towards its coupling product is different from the way towards the side chain-protected peptide of formula IV according to the present invention;
preferably, the side chain-protected peptide of formula IV is

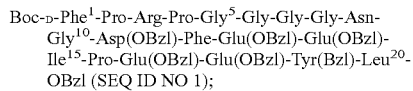
Boc-D-Phe$^1$-Pro-Arg-Pro-Gly$^5$-Gly-Gly-Gly-Asn-Gly$^{10}$-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 1);

as intermediate in a synthesis of bivalirudin of formula

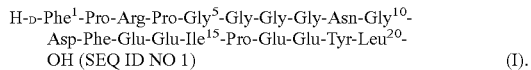
H-D-Phe$^1$-Pro-Arg-Pro-Gly$^5$-Gly-Gly-Gly-Asn-Gly$^{10}$-Asp-Phe-Glu-Glu-Ile$^{15}$-Pro-Glu-Glu-Tyr-Leu$^{20}$-OH (SEQ ID NO 1)   (I).

The present invention also relates to a process for the production of bivalirudin of formula I which comprises the steps of (a) reacting a peptide of formula

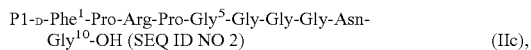
P1-D-Phe$^1$-Pro-Arg-Pro-Gly$^5$-Gly-Gly-Gly-Asn-Gly$^{10}$-OH (SEQ ID NO 2)   (IIc), wherein P1 is a protecting group,
with a peptide of formula

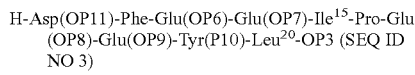
H-Asp(OP11)-Phe-Glu(OP6)-Glu(OP7)-Ile$^{15}$-Pro-Glu(OP8)-Glu(OP9)-Tyr(P10)-Leu$^{20}$-OP3 (SEQ ID NO 3)   (IIIc), wherein P3 and each of P6 through P11 are Bzl,
to yield a peptide of formula

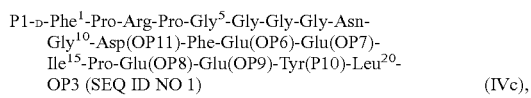
P1-D-Phe$^1$-Pro-Arg-Pro-Gly$^5$-Gly-Gly-Gly-Asn-Gly$^{10}$-Asp(OP11)-Phe-Glu(OP6)-Glu(OP7)-Ile$^{15}$-Pro-Glu(OP8)-Glu(OP9)-Tyr(P10)-Leu$^{20}$-OP3 (SEQ ID NO 1)   (IVc), wherein P1, P3 and P6 through P11 are as defined above;
(b) removing the side chain and C-terminal protecting groups P3 and P6 through P11 of the peptide produced in step (a); and
(c) removing the N-terminal protecting group P1 of the peptide produced in step (b) to yield bivalirudin of formula I.

The process of the present invention allows for a very efficient synthesis of bivalirudin via a convergent fragment synthesis, which can easily be adapted to the production on an industrial scale. Furthermore, this route for the preparation of bivalirudin is very straightforward and does not require the use of a complicated protecting group strategy. In addition, the various building blocks (fragments) are chosen to avoid or minimize racemization during assembly.

Before, during and after the reactions of the present invention, all fragments as well as all coupling products may be present as such or may be present in a suitable salt form depending on the physical-chemical properties of the molecule and/or the reaction conditions. Suitable counter ions are for example the salt forms of triethylamine (TEA), dicyclohexylamine (DCHA), hydrochloric acid (HCl) and trifluoroacetic acid (TFA).

As protecting group P1, any protecting group that is stable to catalytic hydrogenation may be used such as tert-butoxycarbonyl (Boc), fluoren-9-ylmethoxycarbonyl (Fmoc), 2-(3,5-dimethoxyphenyl)prop-2-yloxycarbonyl (Ddz), adamantly-1-oxycarbonyl (Adc), tert-amyloxycarbonyl (Aoc), diphenylphosphinyl (Dpp), 2-(methylsulfonyl)ethoxycarbonyl (Msc) and phthaloyl (Pht). Preferably, the protecting group P1 is Boc, Fmoc or Ddz.

Preferably, the protecting groups P3 and P6 through P11 are benzyl (Bzl). Here and as follows, the abbreviation "OBzl" indicates a benzyl ester (after reaction with a carboxylic acid both of the side chain and the C-terminus), while the abbreviation "Bzl" indicates a benzyl ether (after reaction with e.g. the phenolic hydroxy group of tyrosine).

Steps (a) to (c) can be carried out using standard reaction conditions known in the art of peptide synthesis.

The coupling and deprotection steps (a), (b), and (c) are preferably performed in solution.

For the coupling step (a), DMF is preferably used as solvent. The first deprotection step (b) is preferably performed in acetic acid and/or water, whereas the second deprotection step (c) is preferably carried out in toluene.

In a preferred embodiment, the coupling step (a) is accomplished with a combination of HOBt, EDC.HCl, and TEA.

In a preferred embodiment, the first deprotecting step (b) is carried out with hydrogen gas and palladium on charcoal.

In a preferred embodiment, the second deprotecting step (c) is carried out with TFA. The crude product obtained after step (c) can be purified by conventional methods, e.g. with preparative HPLC, countercurrent distribution or equivalent. The same applies to the intermediates obtained after steps (a) and (b), if purification is required.

The protected peptide fragments IIc and IIIc can be prepared using conventional peptide synthesis methods, e.g. solution phase synthesis (HPPS) or solid phase synthesis (SPPS). In case of SPPS, all resins being known to the person skilled in the art and allowing the preparation of protected peptides can be applied. Here, resins are to be interpreted in a wide manner. Therefore, the term "resin" is to be understood to mean e.g. a solid support alone or a solid support directly linked to a linker, optionally with a handle in between. The resin may be insoluble or soluble. The soluble polymer polyethylene glycol is an example for the solid support of a soluble resin. Preferred resins are polystyrene-based resins with trityl or bromobenzhydryl. Examples for trityl resins are 2-chlorotrityl chloride resin (CTC resin), trityl chloride resin, 4-methyltrityl chloride resin and 4-methoxytrityl chloride resin. Preferably, the CTC resin is applied for the synthesis of fragments containing a free carboxylic function.

In a preferred embodiment, the protected peptide fragments IIc and IIIc are prepared using solution phase synthesis.

Another object of the present invention is to provide protected peptides which are useful as intermediates in the process of the invention. In particular, one of these peptides is a protected peptide of formula IVc, wherein P1 is a protecting group; preferably P1 is Boc; or H; and P3 and P6 through P11 are Bzl.

Another peptide, which is particularly useful as an intermediate in the process of the invention, is an N-terminally protected peptide of formula IIc, wherein P1 is a protecting group, preferably P1 is Boc.

In a further aspect, the present invention also relates to a process for the production of an N-terminally protected peptide of formula P1-D-Phe$^1$-Pro-Arg-Pro-Gly$^5$-Gly-Gly-Gly-Asn-Gly$^{10}$-OH (SEQ ID NO 2)     (IIc), wherein P1 is Boc,
comprising:
(a) removing the C-terminal protecting group of a peptide of formula P1-D-Phe$^1$-Pro-Arg-Pro-OP13 (SEQ ID NO 4)     (Vc), wherein P1 is Boc and P13 is a protecting group such as Bzl, methyl (Me) and ethyl (Et); preferably P13 is Bzl;
to yield an N-terminally protected, C-terminally unprotected peptide of formula Vc with P13 being H;
(b) removing the N-terminal protecting group of a peptide of formula P15-Gly$^5$-Gly-Gly-Gly-Asn-Gly$^{10}$-OBzl (SEQ ID NO 5)     (VIc), wherein P15 is Boc,
to yield a C-terminally protected, N-terminally unprotected peptide of formula VIc with P15 being H;
(c) reacting the peptide of formula Vc produced in step (a), wherein P13 is H, with the peptide of formula VIc produced in step (b), wherein P15 is H,
to yield a peptide of formula P1-D-Phe$^1$-Pro-Arg-Pro-Gly$^5$-Gly-Gly-Gly-Asn-Gly$^{10}$-OBzl (SEQ ID NO 2)     (VIIc), wherein P1 is Boc; and
(d) removing the C-terminal protecting group of the peptide produced in step (c) to yield the N-terminally protected peptide of formula IIc.

Steps (a) to (d) can be carried out using standard reaction conditions known in the art of peptide synthesis.

The coupling and deprotection steps (a), (b), (c), and (d) are preferably performed in solution.

For the coupling step (c), DMF is preferably used as solvent. The first deprotection step (a) is preferably performed in acetone, whereas the second deprotection step (b) is preferably carried out in toluene and/or THF. The third deprotection step (d) is preferably performed in a solvent selected from the group consisting of DMF, acetone, water and a mixture of acetone and water.

In a preferred embodiment, the first deprotecting step (a) is carried out with hydrogen gas and palladium on charcoal.

In a preferred embodiment, the second deprotecting step (b) is carried out with TFA.

In a preferred embodiment, the coupling step (c) is accomplished with a combination of HOBt, DIC and TEA.

In a preferred embodiment, the third deprotecting step (d) is carried out with hydrogen gas and palladium on charcoal.

The crude product obtained after step (d) can be purified by conventional methods, e.g. with preparative HPLC, counter-current distribution or equivalent. The same applies to the intermediates obtained after steps (a), (b) and (c), if purification is required.

The protected peptide fragments Vc and Vic can be prepared using conventional peptide synthesis methods, e.g. solution phase synthesis (HPPS) or solid phase synthesis (SPPS). In case of SPPS, all resins being known to the person skilled in the art and allowing the preparation of protected peptides can be applied. Here, resins are to be interpreted in a wide manner. Therefore, the term "resin" is to be understood to mean e.g. a solid support alone or a solid support directly linked to a linker, optionally with a handle in between. The resin may be insoluble or soluble. The soluble polymer polyethylene glycol is an example for the solid support of a soluble resin, thus leading to a soluble peptide-resin conjugate. Preferred resins are polystyrene-based resins with trityl or bromobenzhydryl. Examples for trityl resins are 2-chlorotrityl chloride resin (CTC resin), trityl chloride resin, 4-methyltrityl chloride resin and 4-methoxytrityl chloride resin. Preferably, the CTC resin is applied for the synthesis of fragments containing a free carboxylic function.

In a preferred embodiment, the protected peptide fragments Vc and Vic are prepared using solution phase synthesis.

Another object of the present invention is to provide protected peptides which are useful as intermediates in the process of the invention for the production of an N-terminal protected peptide of formula IIc. In particular, one of these peptides is the C- and N-terminally protected peptide of formula Vc, wherein P13 is a protecting group, preferably Bzl. Another of these peptides is an N-terminally protected peptide of formula Vc with the free C-terminus.

Another peptide, which is particularly useful as an intermediate in the process of the invention, is a C-terminally protected peptide of formula Vic, wherein P15 is Boc; or P15 is H.

Another peptide, which is particularly useful as an intermediate in the process of the invention, is a C- and N-terminally protected peptide of formula VIIc, wherein P1 is a protecting group, preferably P1 is Boc.

Another peptide, which is particularly useful as an intermediate in the process for the production of bivalirudin, is a protected peptide of formula IIIc, wherein P3 and P6 through P11 are Bzl.

In a further aspect, the present invention also relates to a process for the production of a protected peptide of formula H-Asp(OP11)-Phe-Glu(OP6)-Glu(OP7)-Ile$^{15}$-Pro-Glu(OP8)-Glu(OP9)-Tyr(P10)-Leu$^{20}$-OP3 (SEQ ID NO 3)     (IIIc), wherein P3 and P6 through P11 are Bzl,
comprising:
(a) removing the N-terminal protecting group of a peptide of formula P16-Glu(OP8)-Glu(OP9)-Tyr(P10)-Leu$^{20}$-OP3 (SEQ ID NO 6)     (VIIIc), wherein P3 and P8 through P10 are Bzl and P16 is Boc, to yield a C-terminally protected, N-terminally unprotected peptide of formula VIIIe with P16 being H;
(b) reacting the peptide of formula VIIIc produced in step (a), wherein P16 is H and P3 and P8 through P10 are Bzl, with a peptide of formula P17-Glu(OP6)-Glu(OP7)-Ile$^{15}$-Pro-OH (SEQ ID NO 7)     (IXc), wherein P17 is Boc; and P6 and P7 are Bzl, to yield a peptide of formula P17-Glu(OP6)-Glu(OP7)-Ile$^{15}$-Pro-Glu(OP8)-Glu(OP9)-Tyr(P10)-Leu$^{20}$-OP3 (SEQ ID NO 8)     (Xc), wherein P17 is Boc; and P3 and P6 through P10 are Bzl;

(c) removing the N-terminal protecting group of the peptide of formula Xc produced in step (b), wherein P3 and P6 through P10 are Bzl; and P17 is Boc,
to yield a C-terminally protected, N-terminally unprotected peptide of formula Xc with P3 and P6 through P10 being Bzl and P17 being H;

(d) reacting the peptide of formula Xc produced in step (c), wherein P17 is H; and P3 and P6 through P10 are Bzl, with a protected amino acid of formula Boc-Phe$^{12}$-OH          (XI)

to yield a peptide of formula

P4-Phe-Glu(OP6)-Glu(OP7)-Ile$^{15}$-Pro-Glu(OP8)-Glu
(OP9)-Tyr(P10)-Leu$^{20}$-OP3 (SEQ ID NO 9)     (XIIc), wherein P3 and P6 through P10 are Bzl; and P4 is Boc;

(e) removing the N-terminal protecting group of the peptide of formula XIIc produced in step (d) with P3 and P6 through P10 being Bzl and P4 being Boc,
to yield a C-terminally protected, N-terminally unprotected peptide of formula XIIc with P3 and P6 through P10 being Bzl; and P4 being H;

(f) reacting the peptide of formula XIIc produced in step (e), wherein P4 is H; and P3 and P6 through P10 are Bzl, with a protected amino acid of formula Boc-Asp(OP11)$^{11}$-OH     (XIIIc), wherein P11 is Bzl,
to yield a peptide of formula Boc-Asp(OP11)-Phe-Glu(OP6)-Glu(OP7)-Ile$^{15}$-Pro-
Glu(OP8)-Glu(OP9)-Tyr(P10)-Leu$^{20}$-OP3 (SEQ
ID NO 3)                  (XIVc), wherein P3 and P6 through P11 are Bzl; and (g) removing the N-terminal protecting group of the peptide produced in step (f) to yield the C-terminally protected peptide of formula IIIc.

Steps (a) to (g) can be carried out using standard reaction conditions known in the art of peptide synthesis.

The coupling and deprotection steps (a) to (g) are preferably performed in solution.

For the coupling steps (b), (d) and (f) DMF is preferably used as solvent. The deprotection steps (a), (c), (e) and (g) are preferably performed in a mixture of toluene and THF as solvent.

In a preferred embodiment, the coupling steps (b), (d) and (f) are accomplished with a combination of HOBt, EDC.HCl, and the base TEA for step (b), respectively DIPEA for steps (d) and (f). In another preferred embodiment, the deprotection of steps (a), (c), (e) and (g) is carried out by use of TFA and phenol.

The crude product obtained after step (g) can be purified by conventional methods, e.g. with preparative HPLC, countercurrent distribution or equivalent. The same applies to the intermediates obtained after steps (a) to (f), if purification is required.

The protected peptide fragments VIIIc, IXc, XI, and XIIIc can be prepared using conventional peptide synthesis methods, e.g. solution phase synthesis (HPPS) or solid phase synthesis (SPPS). In case of SPPS, all resins being known to the person skilled in the art and allowing the preparation of protected peptides can be applied. Here, resins are to be interpreted in a wide manner. Therefore, the term "resin" is to be understood to mean e.g. a solid support alone or a solid support directly linked to a linker, optionally with a handle in between. The resin may be insoluble or soluble. The soluble polymer polyethylene glycol is an example for the solid support of a soluble resin. Preferred resins are polystyrene-based resins with trityl or bromobenzhydryl. Examples for trityl resins are 2-chlorotrityl chloride resin (CTC resin), trityl chloride resin, 4-methyltrityl chloride resin and 4-methoxytrityl chloride resin. Preferably, the CTC resin is applied for the synthesis of fragments containing a free carboxylic function.

In a preferred embodiment, the protected peptide fragments VIIIc, IXc, XI, and XIIIc are prepared using solution phase synthesis.

Another object of the present invention is to provide protected peptides which are useful as intermediates in the process of the invention for the production of a C-terminally protected peptide of formula IIIc. In particular, one of these peptides is a protected peptide of formula XIVc, wherein P3 and P6 through P11 are Bzl.

Another peptide, which is particularly useful as an intermediate in the process of the invention, is a side chain-protected peptide of formula XIIc, wherein P3 and P6 through P10 are Bzl; and P4 is the Boc protecting group, or P4 is H.

Another peptide, which is particularly useful as an intermediate in the process of the invention, is a protected peptide of formula Xc, wherein P3 and P6 through P10 are Bzl; and P17 is the Boc protecting group, or P17 is H.

Another peptide, which is particularly useful as an intermediate in the process of the invention, is a protected peptide of formula IXc, wherein P6 and P7 are Bzl; and preferably P17 is Boc.

Another peptide, which is particularly useful as an intermediate in the process of the invention, is a protected peptide of formula VIIIc, wherein P3 and P8 through P10 are Bzl; and P16 is the Boc protecting group, or P16 is H.

In a further aspect, the present invention also relates to the use of any of the above peptides as intermediates in a synthesis of bivalirudin.

EXAMPLES

The following non-limiting examples will illustrate representative embodiments of the invention in detail.

Abbreviations

Boc tert-butoxycarbonyl
Bzl benzyl
DCC 1,3-dicyclohexylcarbodiimide
DCHA dicyclohexylamine
DCU dicyclohexylurea
DIC diisopropylcarbodiimide
DIPEA N,N-diisopropylethylamine
DMF N,N-dimethylformamide
EDC.HCl 1-ethyl-3-(3-dimethylaminopropyl)carbodiimide hydrochloride
equiv. equivalents
HOBt 1-hydroxybenzotriazole
MTBE methyl tert-butyl ether
NMM N-methylmorpholine
HOPfp pentafluorophenol
OPfp pentafluorophenyl ester
HOSu N-hydroxysuccinimide
Su N-succinimidyl
TEA triethylamine
TFA trifluoroacetic acid
THF tetrahydrofuran Example 1

Preparation of H-Asn-Gly$^{10}$-OBzl.TFA

Boc-Asn-Gly-OBzl (90.20 kg; Hexagon Labs Inc., USA) was added at 20° C. to a mixture of TFA (90 L), toluene (388

L) and THF (45 L). TFA (198 L) was slowly added to the mixture at ≤22° C. The reaction was allowed to undergo to completion at 20° C. The completion of the cleavage was monitored by HPLC.

Then, THF was slowly added, and the reaction mixture was evaporated in vacuo. Three azeotropic distillations were performed with a mixture of toluene and THF. H-Asn-Gly[10]-OBzl.TFA was obtained as an oily residue, which was diluted with ethyl acetate. This solution was directly used in the next chemical step (see Example 3).

Yield: 100%. Purity (by HPLC): 99.3%.

Example 2

Preparation of Boc-Gly[5]-Gly-Gly-Gly-OH.TEA (SEQ ID NO 10)

TEA (73.1 L) was slowly added at 20° C. to a suspension of Boc-Gly[5]-Gly-Gly-Gly-OEt (SEQ ID NO 10) [98.11 kg; Bonora et al, *Gazzetta Chimica Italiana* 1980, 110, 503-510, analogously prepared from Boc-Gly-Gly-OH (Senn Chemicals, Switzerland), and H-Gly-Gly-OEt.HCl (Senn Chemicals, Switzerland)] in a mixture of acetone (78.44 L) and processed water (491 L). The reaction was allowed to undergo to completion at 20° C. The completion of the saponification was monitored by HPLC. The solution was evaporated in vacua, and the volume of the residue was adjusted to 456 L with processed water. This solution of Boc-Gly[5]-Gly-Gly-Gly-OH.TEA (SEQ ID NO 10) was directly used in the next chemical step (see Example 3). Yield: 100%. Purity (by HPLC): 99.6%.

Example 3

Preparation of Boc-Gly[5]-Gly-Gly-Gly-Asn-Gly[10]-OBzl (SEQ ID NO 5)

The pH of a solution of H-Asn-Gly[10]-OBzl.TFA (573 L, see Example 1) in ethyl acetate was adjusted to 6-6.5 with TEA at 0° C. The solution of Boc-Gly[5]-Gly-Gly-Gly-OH (SEQ ID NO 10) as obtained from Example 2 was cooled to 0° C. and added, followed by the addition of HOBt (28.52 kg) and EDC HCl (69.81 kg). The pH was adjusted to 6-6.5 with TEA (121 L) at 0° C. The reaction mixture was allowed to warm up to reach room temperature.

On completion of the coupling (after about 10 h; as indicated by HPLC), NaCl was added to the reaction mixture. The suspension was cooled and filtered to give a solid residue, which was washed several times with aqueous NaCl solution and then cooled. The resulting solid was dried in vacuo to give 130.15 kg (100%) of Boc-Gly[5]-Gly-Gly-Gly-Asn-Gly[10]-OBzl(SEQ ID NO 5) with 97.9% purity (by HPLC).

Example 4

Preparation of H-Gly[5]-Gly-Gly-Gly-Asn-Gly[10]-OBzl.TFA (SEQ ID NO 5)

Boc-Gly[5]-Gly-Gly-Gly-Asn-Gly[10]-OBzl (SEQ ID NO 5) (131.20 kg, see Example 3) was slowly added to a mixture of TFA (131 L), toluene (525 L) and THF (105 L) at a temperature of ≤22° C. TFA (289 L) was slowly added to the reaction mixture at a temperature of ≤22° C. The reaction was allowed to go to completion at 20° C. within about 1.5 h (monitored by HPLC).

The reaction mixture was concentrated in vacuo, and the residue was poured into diisopropyl ether. The resulting suspension was filtered to give a solid, which was washed several times with diisopropyl ether and then dried in vacuo to give 130.99 kg H-Gly[n]-Gly-Gly-Gly-Asn-Gly[10]-OBzl.TFA (SEQ ID NO 5) with 97.5% purity (by HPLC).

Example 5

Preparation of H-Arg-Pro-OBzl.2HCl

Hydrochloric acid (1 M) in acetic acid (380 L) was slowly added at ≤22° C. to a suspension of Boc-Arg-Pro-OBzl.HCl (95.00 kg; Hexagon Labs Inc., USA) in acetic acid (190 L) and THF (19 L). The completion of cleavage (after about 1 hour) was monitored by HPLC.

The reaction mixture was evaporated in vacuo. Azeotropic distillations were performed first with acetic acid and then with DMF. The H-Arg-Pro-OBzl.2HCl was afforded as oily residue, which was diluted with DMF to obtain a volume of about 380 L. The resulting solution was directly used in the next chemical step (see Example 7). Yield: 100%. Purity (by HPLC): 96%.

Example 6

Preparation of Boc-D-Phe-Pro-OPfp

A solution of HOPfp (17.78 kg) in ethyl acetate (10 L) was added at ≤24° C. to a suspension of Boc-D-Phe-Pro-OH (33.33 kg; Bachem AG, Switzerland) in ethyl acetate (183 L). A solution of DCC (21.44 kg) in ethyl acetate (83.3 L) was slowly added to the reaction mixture at −6° C. The mixture was then allowed to warm up to room temperature. The coupling completion (about 2 h) was monitored by HPLC.

The DCU salt was removed by filtration and washed with ethyl acetate. The filtrate was evaporated in vacuo until a residual volume of about 80 L was reached. Several azeotropic distillations were performed with toluene. The oily residue was precipitated in petroleum ether. The solid was filtered, washed with petroleum ether and dried in vacuo to obtain 26.3 kg (54%) Boc-D-Phe-Pro-OPfp with 99.3% purity (by HPLC).

Example 7

Preparation of Boc-D-Phe[1]-Pro-Arg-Pro-OBzl.HCl (SEQ ID NO 4)

A solution of H-Arg[3]-Pro-OBzl.2HCl (103.00 kg; 561 L solution; see Example 5) was diluted with DMF (360 L) at 20° C. DMF (82 L) was evaporated in vacuo below 55° C. Boc-D-Phe[1]-Pro-OPfp (121.54 kg; see Example 6) was then added to the solution of H-Arg[3]-Pro-OBzl.2HCl at 20° C. The pH of the resulting mixture was adjusted to 6.5 with TEA (58 L) at 0° C. The reaction was allowed to go to completion at 0° C. for about 20 h, as indicated by HPLC monitoring.

The solid fractions of the resulting suspension were filtered off and washed with DMF. The filtrate was concentrated in vacuo until a residual volume of about 385 L. A mixture of deionized water, NaCl and ethyl acetate was added. The phases were separated and the organic phase was successively washed with aqueous NaHCO$_3$, with aqueous Na$_2$CO$_3$, with a solution of HCl in brine, and finally with brine. The organic phase was concentrated in vacuo to give an oily residue, which was dried by azeotropic distillation with toluene and precipitated in diisopropyl ether at 20° C. The resulting suspension was filtered to afford a solid, which was washed several times with diisopropyl ether and dried in vacuo to give 106 kg of Boc-D-Phe$^1$-Pro-Arg-Pro-OBzl-HCl (SEQ ID NO 4) with 96% purity (by HPLC).

Example 8

Preparation of Boc-D-Phe$^1$-Pro-Arg-Pro-OH (SEQ ID NO 4)

The pH of a solution of Boc-D-Phe$^1$-Pro-Arg-Pro-OBzl.HCl (SEQ ID NO 4) (33.58 kg, see Example 7) in acetone (67 L) was adjusted to 4 with a mixture of TFA/THF (50/50, V/V, 0.03 L) at 20° C. The resulting mixture was added to a suspension of palladium on charcoal (3.36 kg) in acetone (17 L). Hydrogenation was performed at 20° C. for at least 2 h at about 3 bar of hydrogen pressure. The completion of hydrogenation was monitored by HPLC.

The reaction mixture was filtered over cellulose cartridge. The filter cake was washed several times with acetone. The combined filtrates were concentrated in vacuo. The resulting oily residue was dried by azeotropic distillation using a mixture of acetone and toluene. The oily residue was diluted with ethyl acetate and poured into diisopropyl ether. The resulting suspension was filtered and the precipitate was washed several times with diisopropyl ether and dried in vacuo to give 31.4 kg of Boc-D-Phe$^1$-Pro-Arg-Pro-OH (SEQ ID NO 4) with a purity of 99.4% (by HPLC).

Example 9

Preparation of Boc-D-Phe$^1$-Pro-Arg-Pro-Gly$^5$-Gly-Gly-Gly-Asn-Gly$^{10}$-OBzl (SEQ ID NO 2)

The pH of a solution of H-Gly$^5$-Gly-Gly-Gly-Asn-Gly$^{10}$-OBzl TFA (SEQ ID NO 5) (25.20 kg, see Example 4) in DMF (504 L) and deionized water (25 L) was adjusted to 6.5-7 using TEA (9 L) at ≤22° C. Boc-D-Phe$^1$-Pro-Arg-Pro-OH (SEQ ID NO 4) (25.46 kg, see Example 8) and HOBt (1.02 kg) were slowly added at ≤22° C. DIC (9.5 L) was slowly added to the reaction mixture at ≤12° C. The pH of the resulting mixture was adjusted to 7-7.5 using TEA (0.3 L) at ≤12° C. The reaction was allowed to go to completion for 10 days at 10° C., as monitored by HPLC and TLC.

The reaction mixture was concentrated in vacuo to give an oily residue, which was precipitated in a mixture of ethyl acetate and diisopropyl ether. The supernatant liquid was removed several times and replaced by the same volume of diisopropyl ether. The mixture was filtered to give a solid, which was washed three times with diisopropyl ether and dried in vacuo to give 30.50 kg (76%) of Boc-D-Phe$^1$-Pro-Arg-Pro-Gly$^5$-Gly-Gly-Gly-Asn-Gly$^{10}$-OBzl (SEQ ID NO 2) with 83.4% purity (by HPLC).

Example 10

Preparation of Boc-D-Phe$^1$-Pro-Arg-Pro-Gly$^5$-Gly-Gly-Gly-Asn-Gly$^{10}$-OH (SEQ ID NO 2)

A solution of Boc-D-Phe$^1$-Pro-Arg-Pro-Gly$^5$-Gly-Gly-Gly-Asn-Gly$^{10}$-OBzl (SEQ ID NO 2) (23.43 kg net peptide weight, see Example 9) in a mixture of acetone (43 L) and deionized water (9 L) was added to a suspension of palladium on charcoal (0.75 kg) in acetone (3 L). Hydrogenation was performed at 20° C. for 11 h at about 3 bar hydrogen pressure. The completion of hydrogenation was monitored by HPLC.

Deionized water (36 L) was added to the reaction mixture and the resulting mixture was filtered over cellulose cartridge. The filter cake was washed several times with a 2:8 mixture of deionized water and acetone. The combined filtrates were concentrated in vacuo. The resulting residue was dried by azeotropic distillation using a mixture of DMF and toluene to give 21.5 kg of Boc-D-Phe$^1$-Pro-Arg-Pro-Gly$^5$-Gly-Gly-Gly-Asn-Gly$^{10}$-OH (SEQ ID NO 2) with 80% purity (by HPLC).

Example 11

Preparation of Boc-Tyr(Bzl)-Leu$^{20}$-OBzl

H-Leu-OBzl.p-tosylate (22.2 kg; Bachem AG, Switzerland) was suspended in ethyl acetate (108 L), then TEA (about 7.1 L) was added at room temperature. Boc-Tyr(Bzl)-OH (20 kg; Senn Chemicals, Switzerland) and HOBt (7.3 kg) were added as solids. A solution of DCC (12.2 kg) in DMF (40 L) was added to the mixture at −6° C. The completion of the reaction was monitored by TLC and HPLC.

The formed DCU was removed by filtration. The filtrate was successively washed with a mixture of aqueous KHSO$_4$ solution and brine; aqueous KHSO$_4$ solution; aqueous NaHCO$_3$ solution and with brine. The organic phase was evaporated in vacuo. The residue was dissolved in ethyl acetate, and then precipitated in petroleum ether. The solid was filtered, washed with petroleum ether and dried in vacuo. A second crop was obtained after mother liquor solution concentration in vacuo and precipitation in petroleum ether. The solid was filtered, washed with petrolum ether and dried in vacuo. The two crops were then mixed, yielding 25.9 kg (84%) of Boc-Tyr(Bzl)-Leu$^{20}$-OBzl with 97% purity (by HPLC).

Example 12

Preparation of H-Tyr(Bzl)-Leu$^{20}$-OBzl.TFA

TFA (83 L) was slowly added at 20° C. to a mixture of Boc-Tyr(Bzl)-Leu$^{20}$-OBzl (25.9 kg, see Example 11), phenol (1.3 kg), toluene (104 L) and THF (21 L). The reaction was allowed to undergo to completion at 20° C. The completion of the cleavage was monitored by HPLC.

The reaction mixture was evaporated in vacuo. An azeotropic distillation was performed with a mixture of toluene and THF. Then, ethyl acetate and petroleum ether were added to the residue. The solid was filtered, washed with a mixture of ethyl acetate and petroleum ether, then with petroleum ether, and finally dried in vacuo, yielding 23.7 kg (89%) of H-Tyr(Bzl)-Leu$^{20}$-OBzl.TFA with 98% purity (by HPLC).

Example 13

Preparation of Boc-Glu(OBzl)-Glu(OBzl)-Tyr(Bzl)-Leu$^{20}$-OBzl (SEQ ID NO 6)

Boc-Glu(OBzl)-Glu(OBzl)-OSu (42.90 kg, Senn Chemicals, Switzerland) was added to a solution of H-Tyr(Bzl)-Leu-OBzl.TFA (23.7 kg, see Example 12) in DMF (80 L). The pH of the reaction mixture was slowly adjusted to 7-7.5 with DIPEA at 0° C. The reaction mixture was allowed to undergo to completion at 20° C. The completion of the coupling was monitored by HPLC.

The reaction mixture was evaporated in vacuo, and the oily residue was poured into processed water. The solid was filtered, washed with processed water, re-slurried in a mixture of acetonitrile and processed water and finally dried in vacuo, yielding 40.3 kg of Boc-Glu(OBzl)-Glu(OBzl)-Tyr(Bzl)-Leu$^{20}$-OBzl (SEQ ID NO 6) with 92% purity (by HPLC).

Example 14

Preparation of H-Glu(OBzl)-Glu(OBzl)-Tyr(Bzl)-Leu[20]-OBzl.TFA (SEQ ID NO 6)

Boc-Glu(OBzl)-Glu(OBzl)-Tyr(Bzl)-Leu[20]-OBzl (SEQ ID NO 6) (117.45 kg, see Example 13) was slowly added at 15° C. to a mixture of TFA (117 L), phenol (5.87 kg), toluene (470 L) and THF (94 L). Additional TFA (282 L) was slowly added to the mixture at ≤17° C. The reaction was allowed to undergo to completion at 15° C. The cleavage completion (3 h) was monitored by HPLC.

The reaction mixture was evaporated in vacuo below 35° C. Residual TFA was removed by azeotropic distillations with a mixture of toluene/THF and then with toluene. MTBE (825 L) was added to the oily residue. Then, petroleum ether was added to the obtained suspension. After cooling, the solid was filtered and washed several times with petroleum ether. After re-suspension in petroleum ether and filtration, the solid was washed with petroleum ether. This procedure was repeated once. The solid was then dried in vacuo yielding 114.86 kg (96%) of H-Glu(OBzl)-Glu(OBzl)-Tyr(Bzl)-Leu[20]-OBzl.TFA (SEQ ID NO 6) with 96% purity (by HPLC).

Example 15

Preparation of Boc-Glu(OBzl)-Glu(OBzl)-Ile[15]-Pro-OH.DCHA (SEQ ID NO 7)

Boc-Glu(OBzl)-Glu(OBzl)-OSu (62 kg, Senn Chemicals, Switzerland) was slowly added to a solution of H-Ile-Pro-OH.TFA (36 kg, Bachem AG, Switzerland) in DMF (433 L). The pH was adjusted to 7-7.5 with DIPEA at 0° C. The completion of the reaction was monitored by HPLC.

The reaction mixture was evaporated in vacuo and the oily residue was diluted with ethyl acetate. The mixture was washed with aqueous KHSO$_4$ solution and with brine. The organic layer was evaporated in vacuo and the oily residue was dried by azeotropic distillations with toluene. The oily residue was diluted with toluene, and the pH was adjusted to 7-7.5 with DCHA. Petroleum ether was then added to the mixture. The solid thus obtained was filtered, washed with petroleum ether and dried in vacuo, yielding 102 kg of Boc-Glu(OBzl)-Glu(OBzl)-Ile[15]-Pro-OH.DCHA (SEQ ID NO 7) with 89% purity (by HPLC).

Example 16

Preparation of Boc-Glu(OBzl)-Glu(OBzl)-Ile[15]-Pro-Glu(OBzl)-Glu(OBzl)-Tyr(Bzl)-Leu[20]-OBzl (SEQ ID NO 8)

Boc-Glu(OBzl)-Glu(OBzl)-Ile[15]-Pro-OH DCHA (SEQ ID NO 7) (98.88 kg, see Example 15) and HOBt (13.82 kg) were slowly added at 524° C. to a solution of H-Glu(OBzl)-Glu(OBzl)-Tyr(Bzl)-Leu[20]-OBzl.TFA (SEQ ID NO 6) (110.39 kg, net peptide weight, see Example 14) in DMF (451 L). EDC.HCl (22.99 kg) was added by small portions to the mixture at −6° C. The pH of the reaction mixture was adjusted to 6.5-7 with TEA (12 L) at −6° C. The coupling was allowed to undergo to completion at 10° C. for 16 h as monitored by HPLC.

The salts were removed by filtration. The filtrate was evaporated in vacuo. The oily residue (470 L) was precipitated in a NaHCO$_3$ solution. The solid was filtered and washed several times with processed water. After re-suspension in processed water, acetonitrile was added. Then, the suspension was cooled down. The solid was filtered, washed with water and dried in vacuo yielding 160.34 kg (88%) of Boc-Glu(OBzl)-Glu(OBzl)-Ile[15]-Pro-Glu(OBzl)-Glu(OBzl)-Tyr(Bzl)-Leu[20]-OBzl (SEQ ID NO 8) with 90% purity (by HPLC).

Example 17

Preparation of H-Glu(OBzl)-Glu(OBzl)-Ile[15]-Pro-Glu(OBzl)-Glu(OBzl)-Tyr(Bzl)-Leu[20]-OBzl.TFA (SEQ ID NO 8)

Boc-Glu(OBzl)-Glu(OBzl)-Ile[15]-Pro-Glu(OBzl)-Glu(OBzl)-Tyr(Bzl)-Leu[20]-OBzl (SEQ ID NO 8) (72.24 kg, see Example 16) was added at ≤15° C. to a mixture of TFA (72 L), toluene (289 L) and THF (6 L). Additional TFA (159 L) was slowly added to the mixture at ≤22° C. The reaction was allowed to undergo to completion at 20° C. for 2.5 h (monitored by HPLC). The reaction mixture was evaporated in vacuo. Residual TFA was removed by several azeotropic distillations with a mixture of toluene and THF. The oily residue was diluted with toluene and poured into diisopropyl ether. The solid was filtered and washed several times with diisopropyl ether. After re-suspension in a mixture of acetonitrile and diisopropyl ether, the solid was then filtered, washed several times with diisopropyl ether and finally dried in vacuo yielding 61.7 kg (87%) of H-Glu(OBzl)-Glu(OBzl)-Ile[15]-Pro-Glu(OBzl)-Glu(OBzl)-Tyr(Bzl)-Leu[20]-OBzl.TFA (SEQ ID NO 8) with 88.9% purity (by HPLC).

Example 18

Preparation of Boc-Phe-Glu(OBzl)-Glu(OBzl)-Ile[15]-Pro-Glu(OBzl)-Glu(OBzl)-Tyr(Bzl)-Leu[20]-OBzl (SEQ ID NO 9)

Boc-Phe-OH (10.03 kg; Senn Chemicals AG, Switzerland) and HOBt (4.95 kg) were slowly added at ≤24° C. to a solution of H-Glu(OBzl)-Glu(OBzl)-Ile[15]-Pro-Glu(OBzl)-Glu(OBzl)-Tyr(Bzl)-Leu[20]-OBzl.TFA (SEQ ID NO 8) (61.63 kg, see Example 17) in DMF (264 L). EDC.HCl (8.53 kg) was slowly added at −5° C. The pH of the reaction mixture was progressively adjusted to 6.5-7 with DIPEA (47.5 L) at −5° C. The coupling was allowed to undergo to completion at 10° C. for 23 h (monitored by HPLC). The reaction mixture was evaporated in vacuo. The oily residue was suspended in a NaHCO$_3$ solution. The solid was filtered, washed several times with processed water and dried in vacuo yielding 67.64 kg (95%) of Boc-Phe-Glu(OBzl)-Glu(OBzl)-Ile[15]-Pro-Glu(OBzl)-Glu(OBzl)-Tyr(Bzl)-Leu[20]-OBzl (SEQ ID NO 9) with 87.9% purity (by HPLC).

Example 19

Preparation of H-Phe-Glu(OBzl)-Glu(OBzl)-Ile[15]-Pro-Glu(OBzl)-Glu(OBzl)-Tyr(Bzl)-Leu[20]-OBzl.TFA (SEQ ID NO 9)

Boc-Phe-Glu(OBzl)-Glu(OBzl)-Ile[15]-Pro-Glu(OBzl)-Glu(OBzl)-Tyr(Bzl)-Leu[20]-OBzl (SEQ ID NO 9) (67.66 kg, see Example 18) was added by small portions at 15° C. to a mixture of TFA (68 L), phenol (3.38 kg), toluene (271 L) and THF (54 L). Additional TFA (149 L) was slowly added to the mixture at 15° C. The cleavage completion (4.3 h) was monitored by HPLC.

The reaction mixture was evaporated in vacuo. Residual TFA was removed by several azeotropic distillations with a mixture of toluene and THF. The oily residue was diluted with toluene and poured into diisopropyl ether. The solid was filtered, washed several times with diisopropyl ether and dried in vacua yielding 67.25 kg (99%) of H-Phe-Glu(OBzl)-Glu(OBzl)-Ile$^{15}$-Pro-Glu(OBzl)-Glu(OBzl)-Tyr(Bzl)-Leu$^{20}$-OBzl. (SEQ ID NO 9) with 86.6% purity (by HPLC).

Example 20

Preparation of Boc-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 3)

Boc-Asp(OBzl)$^{11}$-OH (20.22 kg) (Senn Chemicals AG, Switzerland) and HOBt (8.42 kg) were added in small portions to a solution of H-Phe-Glu(OBzl)-Glu(OBzl)-Ile$^{15}$-Pro-Glu(OBzl)-Glu(OBzl)-Tyr(Bzl)-Leu$^{20}$-OBzl TFA (SEQ ID NO 9) (60.46 kg net peptide weight, see Example 19) in DMF (370 L) at ≤20° C. EDC.HCl (13.38 kg) was slowly added to the reaction mixture at −5° C. The pH of the resulting mixture was progressively adjusted to 6.5-7 with DIPEA (27 L) at −5° C. The coupling reaction was then allowed to go to completion for 35 h at 10° C. (monitored by HPLC).

The reaction mixture was then concentrated in vacuo. The resulting oily residue was slowly added to an aqueous NaHCO$_3$ solution. The resulting suspension was filtered and re-suspended in deionized water. After filtration and several washings with deionized water and once with a mixture of acetonitrile and deionized water, the resulting solid was dried in vacua yielding 64 kg (96%) of Boc-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 3) with 81.4% purity (by HPLC).

Example 21

Preparation of H-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl.TFA (SEQ ID NO 3)

Boc-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl(SEQ ID NO 3) (64.00 kg, see Example 20) was added in small portions to a mixture of TFA (64 L), phenol (3.2 kg), toluene (265 L), and THF (51 L) at a temperature below 15° C. Additional TFA (141 L) was slowly added to the reaction mixture at ≤15° C. The cleavage was performed at 15° C. for 4.8 h (monitored by HPLC).

The reaction mixture was concentrated in vacuo. The resulting oily residue was added to diisopropyl ether for precipitation at 20° C. The resulting suspension was filtered, re-suspended in diisopropyl ether and filtered again. The solid was washed with diisopropyl ether and dried in vacuo yielding 61.4 kg (net peptide weight) (95%) of H-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl. TFA (SEQ ID NO 3) with 77.6% purity (by HPLC).

Example 22

Preparation of Boc-D-Phe$^1$-Pro-Arg-Pro-Gly$^5$-Gly-Gly-Gly-Asn-Gly$^{10}$-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 1)

H-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl TFA (SEQ ID NO 3) (104.40 kg, see Example 21) and HOBt (8.42 kg) were added in small portions to a solution of Boc-D-Phe$^1$-Pro-Arg-Pro-Gly$^5$-Gly-Gly-Gly-Asn-Gly$^{10}$-OH (SEQ ID NO 2) (65.47 kg, see Example 10) in DMF (345 L) at ≤24° C. EDC.HCl (12.46 kg) was slowly added at −5° C. The pH of the reaction mixture was progressively adjusted to 6.5-7 with TEA (16.5 L) at −5° C. The coupling was allowed to go to completion for 22 h at −5° C. (monitored by HPLC).

The reaction mixture was diluted slowly with deionized water. The resulting suspension was filtered, washed with deionized water and dried in vacuo yielding 72 kg (50%) of Boc-D-$^1$Phe-Pro-Arg-Pro-Gly$^5$-Gly-Gly-Gly-Asn-Gly$^{10}$-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl (SEQ ID NO 1) with 81.4% purity (by HPLC).

Example 23

Preparation of H-D-Phe$^1$-Pro-Arg-Pro-Gly$^5$-Gly-Gly-Gly-Asn-Gly$^{10}$-Asp-Phe-Glu-Glu-Ile$^{15}$-Pro-Glu-Glu-Tyr-Leu$^{20}$-OH.2 TFA (Bivalirudin) (SEQ ID NO 1)

A suspension of Boc-D-Phe$^1$-Pro-Arg-Pro-Gly$^5$-Gly-Gly-Gly-Asn-Gly$^{10}$-Asp(OBzl)-Phe-Glu(OBzl)-Glu(OBzl)-Ile$^{15}$-Pro-Glu(OBzl)-Glu(OBzl)-Tyr(Bzl)-Leu$^{20}$-OBzl(SEQ ID NO 1) (15.00 kg, see Example 22) in acetic acid (53 L) was added to a mixture of palladium on charcoal (1.13 kg), deionized water (6 L) and acetic acid (5 L). Hydrogenation was performed at ≤37° C. under about 3 bar of hydrogen pressure (monitored by HPLC).

After completion (5 h), the reaction mixture was cooled and diluted with deionized water and acetic acid. The resulting mixture was filtered over cellulose cartridge, which was several times eluted with a mixture of acetic acid and processed water. The filtrate was concentrated in vacuo. The resulting residue was tested for its water content by Karl Fischer titration (water content<5.0%).

Then, toluene was added to the oily residue followed by addition of TFA. Completion of the cleavage (after 1 h) was monitored by HPLC.

The reaction mixture was concentrated in vacuo. The resulting oily residue was added to diisopropyl ether for precipitation. The resulting suspension was filtered to give a solid, which was washed several times with diisopropyl ether and dried in vacuo yielding 8.41 kg (net peptide weight) (78%) of crude H-D-Phe$^1$-Pro-Arg-Pro-Gly$^5$-Gly-Gly-Gly-Asn-Gly$^{10}$-Asp-Phe-Glu-Glu-Ile$^{15}$-Pro-Glu-Glu-Tyr-Leu$^{20}$-H.2 TFA (bivalirudin) (SEQ ID NO 1) with a purity of crude bivalirudin of 65% (by HPLC). There was no D-Phe$^{12}$-bivalirudin impurity detected by HPLC, i.e. no racemization occurred at position 12.

The crude peptide was purified by preparative HPLC on a C18 reverse phase stationary phase. In a first step, the crude bivalirudin was purified by gradient elution with ammonium acetate/water/acetonitrile and in a second step by gradient elution with trifluoroacetic acid/water/acetonitrile. The eluate fractions containing pure product were concentrated and lyophilized, yielding 5.89 kg (70%, based on bivalirudin content in the crude peptide) of H-D-Phe$^1$-Pro-Arg-Pro-Gly$^5$-Gly-Gly-Gly-Asn-Gly$^{10}$-Asp-Phe-Glu-Glu-Ile$^{15}$-Pro-Glu-Glu-Tyr-Leu$^{20}$-H.2 TFA (bivalirudin) (SEQ ID NO 1) as a white powder with a purity of 99% (by HPLC). No D-Phe$^{12}$-bivalirudin and no D-Tyr$^{19}$-bivalirudin was detected, and each other impurity detected was not more than 0.2% (by HPLC).

The invention claimed is:

1. A process for the production of bivalirudin of formula

H-D-Phe¹-Pro-Arg-Pro-Gly⁵-Gly-Gly-Gly-Asn-Gly¹⁰-Asp-Phe-Glu-Glu-Ile¹⁵-Pro-Glu-Glu-Tyr-Leu²⁰-OH (SEQ ID NO: 1)　　(I)

comprising the steps of:
(a) reacting an optionally side chain-protected peptide of formula P1-D-Phe¹-Pro-Arg-Pro-OH (SEQ ID NO: 4)　　(V), wherein P1 is a protecting group being stable to catalytic hydrogenation,
with an optionally side chain-protected peptide of formula H-Gly⁵-Gly-Gly-Gly-Asn-Gly¹⁰-OP2 (SEQ ID NO: 5)　　(VI), wherein P2 is a protecting group being removable by catalytic hydrogenation and being orthogonal to the optional side chain protecting group(s),
to produce an optionally side chain-protected peptide of formula P1-D-Phe¹-Pro-Arg-Pro-Gly⁵-Gly-Gly-Gly-Asn-Gly¹⁰-OP2 (SEQ ID NO: 2)　　(VII), wherein P1 and P2 are as defined above,
(b) removing P2 of the peptide produced in step (a) to produce the optionally side chain-protected peptide of formula P1-D-Phe¹-Pro-Arg-Pro-Gly⁵-Gly-Gly-Gly-Asn-Gly¹⁰-OH (SEQ ID NO: 2)　　(II), wherein P1 is as defined above,
(c) reacting a side chain-protected peptide of formula H-Glu-Glu-Ile¹⁵-Pro-Glu-Glu-Tyr-Leu²⁰-OP3 (SEQ ID NO: 8)　　(X), wherein P3 is a protecting group being removable by catalytic hydrogenation, with a phenylalanine of formula P4-Phe¹²-OH　　(XI), wherein P4 is a protecting group being orthogonal to the side chain protecting group(s) of the peptide of formula X and to P3,
to produce a side chain-protected peptide of formula P4-Phe-Glu-Glu-Ile¹⁵-Pro-Glu-Glu-Tyr-Leu²⁰-OP3 (SEQ ID NO: 9)　　(XII), wherein P3 and P4 are as defined above,
(d) removing P4 of the peptide produced in step (c) to produce the corresponding N-terminally deprotected, side chain protected peptide of formula XII,
(e) reacting the peptide of formula XII produced in step (d) with a side chain protected aspartic acid of formula P5-Asp¹¹-OH　　(XIII), wherein P5 is a protecting group being orthogonal to the side chain protecting group(s) of the peptide of formula XII, to the side chain protecting group of the amino acid of formula XIII, and to the protecting group P3,
to produce a side chain-protected peptide of formula P5-Asp-Phe-Glu-Glu-Ile¹⁵-Pro-Glu-Glu-Tyr-Leu²⁰-OP3 (SEQ ID NO: 3)　　(XIV), wherein P3 and P5 are as defined above,
(f) removing P5 of the peptide produced in step (e) to produce the side chain-protected peptide of formula H-Asp-Phe-Glu-Glu-Ile¹⁵-Pro-Glu-Glu-Tyr-Leu²⁰-OP3 (SEQ ID NO: 3)　　(III), wherein P3 is as defined above,
(g) reacting the optionally side chain-protected peptide of formula II produced in step (b) with the side chain-protected peptide of formula III produced in step (f) to produce a side chain-protected peptide of formula P1-D-Phe¹-Pro-Arg-Pro-Gly⁵-Gly-Gly-Gly-Asn-Gly¹⁰-Asp-Phe-Glu-Glu-Ile¹⁵-Pro-Glu-Glu-Tyr-Leu²⁰-OP3 (SEQ ID NO: 1)　　(IV), wherein P1 and P3 are as defined above,
(h) removing P1, P3 and the side chain protecting groups of the peptide produced in step (g) to produce bivalirudin of formula I, and wherein steps (a) through (g) are performed in solution phase.

2. The process of claim 1, wherein at least one of P1, P4 and P5 is tert-butoxycarbonyl (Boc), 2-(biphenyl-4-yl)prop-2-yloxycarbonyl (Bpoc), 2-(3,5-di-methoxyphenyl)prop-2-yloxycarbonyl(Ddz), fluoren-9-ylmethoxycarbonyl (Fmoc) or 2-(methylsulfonyl)ethoxycarbonyl (Msc).

3. The process of claim 2, wherein at least one of P1, P4 and P5 is Boc.

4. The process of claim 1, wherein at least one of P2 and P3 is benzyl (Bzl), benzyloxymethyl (Bom), phenacyl (Pac), 4-nitrobenzyl (ONbz), 4-pyridylmethyl (Pic), or 4-sulfobenzyl, with the proviso that, if P4 or P5 is Boc, Bpoc or Ddz, P3 is not Bom.

5. The process of claim 4, wherein at least one of P2 and P3 is Bzl.

6. The process of claim 1, wherein the side chain protected peptides of formula III, IV, X, XII, and XIV and the side chain protected amino acid of formula XIII are protected with at least one side chain protecting group selected from the group consisting of benzyl (Bzl), benzyloxymethyl (Bom), phenacyl (Pac), 4-nitrobenzyl (ONbz), 4-pyridylmethyl (Pic), and 4-sulfobenzyl;
with the proviso that, if P4 or P5 is Boc, Bpoc or Ddz, none of the side chain protecting groups is Bom.

7. The process of claim 6, wherein the side chain protected peptides of formula III, IV, X, XII, and XIV and the side chain protected amino acid of formula XIII are protected with at least one Bzl.

8. The process of claim 1, wherein in step (a) at least one of the optionally side chain-protected peptides of formula V and VI are side chain-unprotected.

9. The process of claim 1, wherein in step (c) the peptide of formula X is of formula H-Glu(OP6)-Glu(OP7)-Ile¹⁵-Pro-Glu(OP8)-Glu(OP9)-Tyr(P10)-Leu²⁰-OP3 (SEQ ID NO: 8)　　(Xb), wherein
P3 is a protecting group being removable by catalytic hydrogenation; and
each of P6 through P10 is independently selected from the group consisting of Bzl, Bom, Pac, ONbz, Pic and 4-sulfobenzyl;
and in step (e) the side chain protected aspartic acid of formula XIII is P5-Asp(OP11)¹¹-OH, wherein
P5 is a protecting group being orthogonal to the side chain protecting group(s) of the peptide of formula XII, to the side chain protecting group of the amino acid of formula XIII, and to the protecting group P3; and
P11 is selected from the group consisting of Bzl, Bom, Pac, ONbz, Pic and 4-sulfobenzyl.

10. The process of claim 9, wherein P3 is Bzl, Bom, Pac, ONbz, Pic or 4-sulfobenzyl; each of P6 through P10 is independently Bzl, Bom, Pac, ONbz, Pic or 4-sulfobenzyl; P5 is Boc, Bpoc, Ddz, Fmoc or Msc; and P11 is Bzl, Bom, Pac, ONbz, Pic or 4-sulfobenzyl.

11. The process of claim 10, wherein P3 is Bzl; each of P6 through P10 is Bzl; P5 is Boc; and P11 is Bzl.

12. The process of claim 9, wherein P1, P4 and P5 are Boc; and P2, P3, P6, P7, P8, P9, P10 and P11 are Bzl.

13. The process of claim 1, wherein in step (h), first P3 and the side chain protecting group(s) are removed simultaneously, and P1 is removed afterwards.

14. The process of claim 13, wherein the peptide, obtained after simultaneous removing P3 and the side chain protecting group(s), is not isolated before removing P1.

15. The process of claim 1, wherein at least one of the removal steps (b) and (h) is carried out in a solvent with hydrogen gas and palladium on charcoal.

16. The process of claim 15, wherein the solvent is selected from the group consisting of N,N-dimethylformamide, acetone, a mixture of acetone and water, acetic acid, and a mixture of acetic acid and water.

17. The process of claim 1, wherein at least one of the peptides selected from the group consisting of the optionally side chain-protected peptide of formula V, the optionally side chain-protected peptide of formula VI and the side chain-protected peptide of formula X is prepared by solution phase synthesis in a preceding process.

18. The process of claim 1, wherein at least one of the peptides selected from the group consisting of the optionally side chain-protected peptide of formula V, the optionally side chain-protected peptide of formula VI and the side chain-protected peptide of formula X is prepared by solid phase synthesis in a preceding process.

* * * * *